(12) United States Patent
Vallera et al.

(10) Patent No.: US 7,101,542 B1
(45) Date of Patent: Sep. 5, 2006

(54) CELL-MEDIATED TARGETING OF TOXINS TO PATHOGENIC CELLS

(76) Inventors: Daniel A. Vallera, 8116 W. Franklin Ave., St. Louis Park, MN (US) 55426; Bruce R. Blazar, 4350 Sussex Rd., Golden Valley, MN (US) 55416

( * ) Notice: Subject to any disclaimer, the term of this patent is extended or adjusted under 35 U.S.C. 154(b) by 0 days.

(21) Appl. No.: 09/579,738

(22) Filed: May 26, 2000

Related U.S. Application Data

(60) Provisional application No. 60/136,014, filed on May 26, 1999.

(51) Int. Cl.
  *A61K 48/00* (2006.01)
  *A01N 63/00* (2006.01)
  *C12N 15/74* (2006.01)
  *C12N 15/09* (2006.01)
  *C12P 21/06* (2006.01)

(52) U.S. Cl. .................. 424/93.21; 424/93.1; 424/93.2; 435/69.1; 435/320.1; 435/455; 514/44

(58) Field of Classification Search ............... 424/93.1, 424/130.1, 93.21, 93.2; 514/44; 435/320.1, 435/69.1, 325, 455
See application file for complete search history.

(56) References Cited

U.S. PATENT DOCUMENTS 5,736,387 A * 4/1998 Paul et al. ................ 435/320.1
6,001,329 A * 12/1999 Buchsbaum et al. ....... 424/1.41

FOREIGN PATENT DOCUMENTS

EP    WO 98/17116    4/1998

OTHER PUBLICATIONS

Verma et al., Gene therapy-promises, problems and prospects, 1997, NATURE, vol. 389, pp. 239-242.*
Deonarain, Ligand-targeted receptor-mediated vectors for gene delivery, 1998, Exp. Opin. Ther. Patents, vol. 8, pp. 53-69.*
Crystal, Transfer of genes to humans: early lessons and obstacles to success, 1995, SCIENCE, vol. 270, pp. 404-410.*
Miller et al., Targeted vectors for gene therapy, 1995, FASEB, pp. 190-199.*
Cochlovius et al, Cancer Immunol Immunother 1998;46:61-6.*
Debinski et al, J Bio Chem 1993;268:14065-70.*
Clay et al, Pathol Oncol Res Jan. 1999;5:3-15.*
Kreitman et al, Int J Immunopharm 1992;14:465-72.*
Moreck et al, Cancer Immunol Immunother,1991;32:342-352.*
Heslop et al, Curr Opin Hematol 1995;2:417-22.*
Sweeney et al, Bioconj Chem 1998;9:201-7.*
Boyer et al., "The Role of B7 Costimulation by Murine Acute Myeloid Leukemia in the Generation and Function of a CD8+ T-Cell Line With Potent In Vivo Graft-Versus-Leukemia Properties," Blood 89(9):3477-3485, 1997.
Chung-Huang Chan et al., "Reactivity of Murine Cytokine Fusion Toxin, Diphtheria Toxin$_{390}$-Murine Interleukin-3 (DT$_{390}$-mIL-3), with Bone Marrow Progenitor Cells," Blood 88(4):1445-1456, 1996.
Chung-Huang Chan et al., "A Murine Cytokine Fusion Toxin Specifically Targeting the Murine Granulocyte-Macrophage Colony-Stimulating Factor . . . Receptor on Normal Committed Bone Marrow Progenitor Cells and GM-CSF-Dependent Tumor Cells," Blood 86(7):2732-2740, 1995.
Si-Yi Chen, "A Novel Artificial Tumor-Specific Killer Cell and Intrabody Approaches for Cancer Therapy," Chapter 25, pp. 389-396, In *Gene Therapy of Cancer*, Academic Press, 1999.
Si-Yi Chen et al., "Potent antitumour activity of a new class of tumour-specific killer cells," Nature 385:78-80, 1997.
An-Gan Yang et al., "A new class of antigen-specific killer cells," Nature Biotechnology 15:46-51, 1997.

* cited by examiner

*Primary Examiner*—Q. Janice Li
(74) *Attorney, Agent, or Firm*—Fish & Richardson P.C.

(57) ABSTRACT

The invention features vectors encoding immunotoxic fusion proteins containing targeting domains and toxic domains, targeting cells transduced with the vectors, methods of making the targeting cells, and methods of treating diseases (e.g., cancer) using both the vectors and the transduced cells.

25 Claims, 16 Drawing Sheets

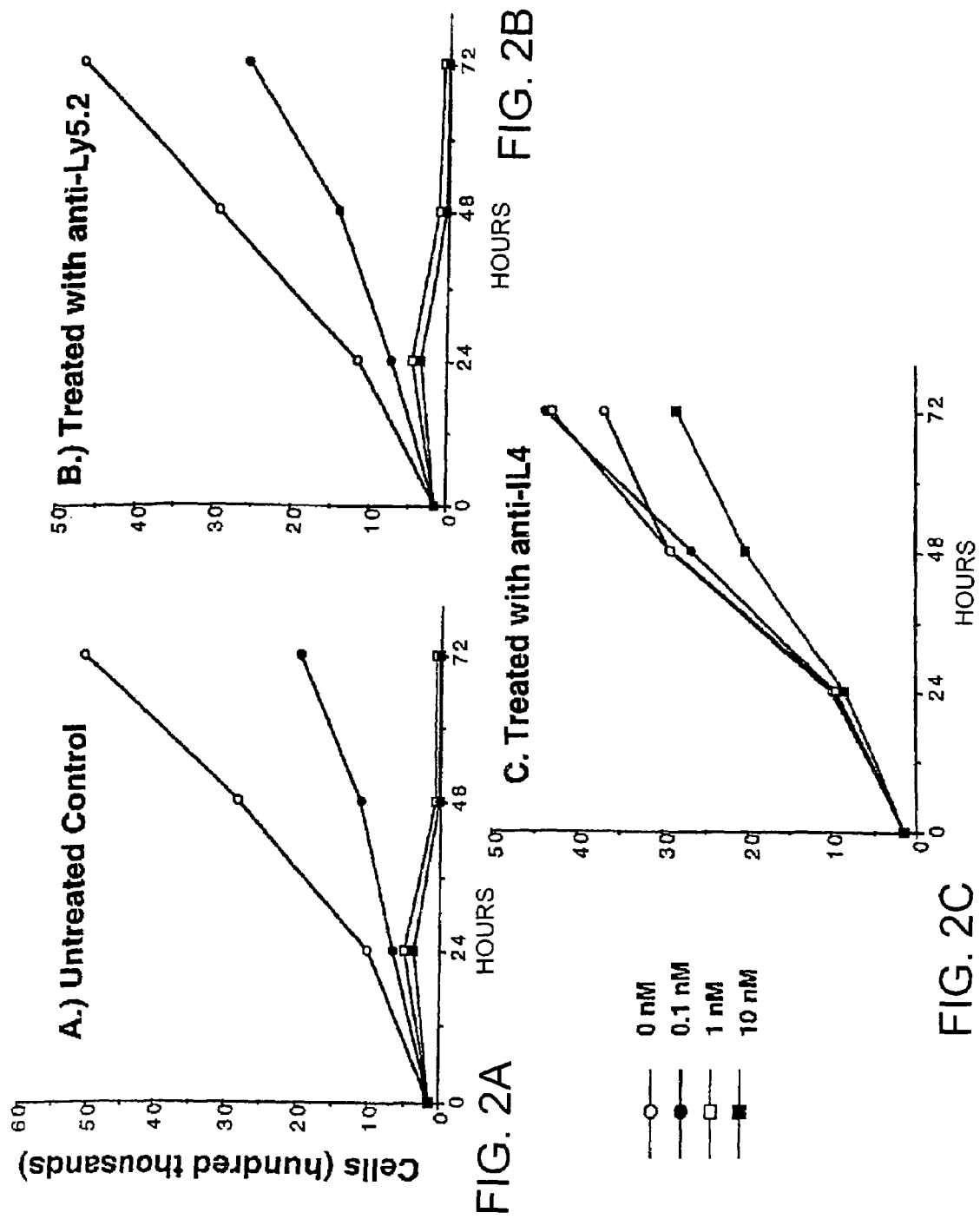

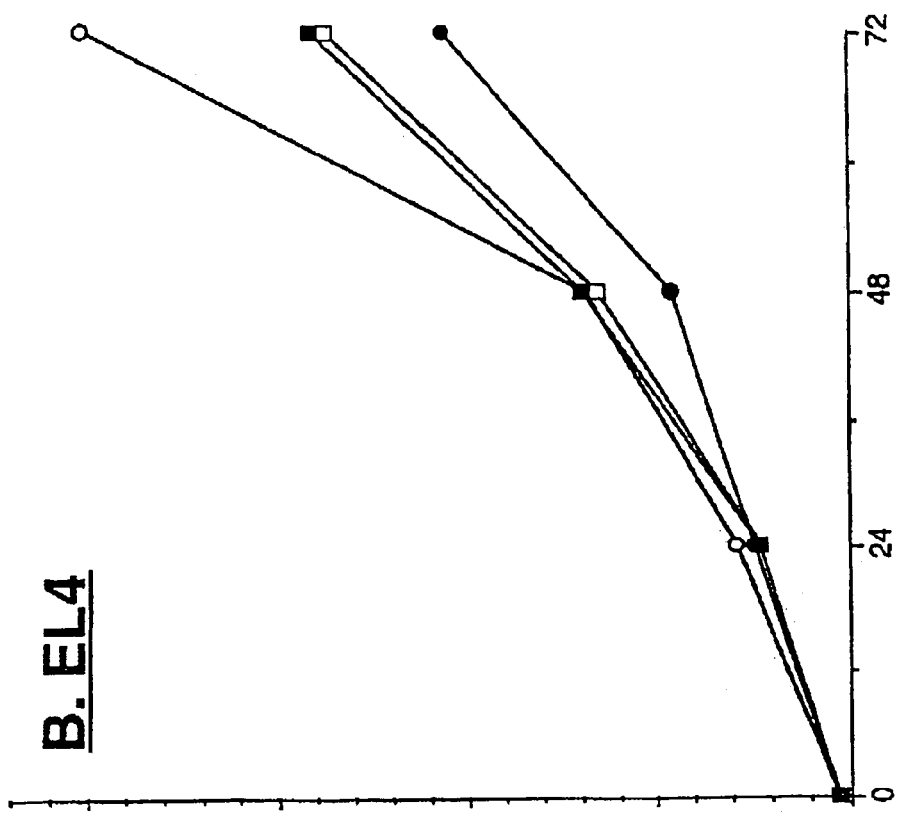
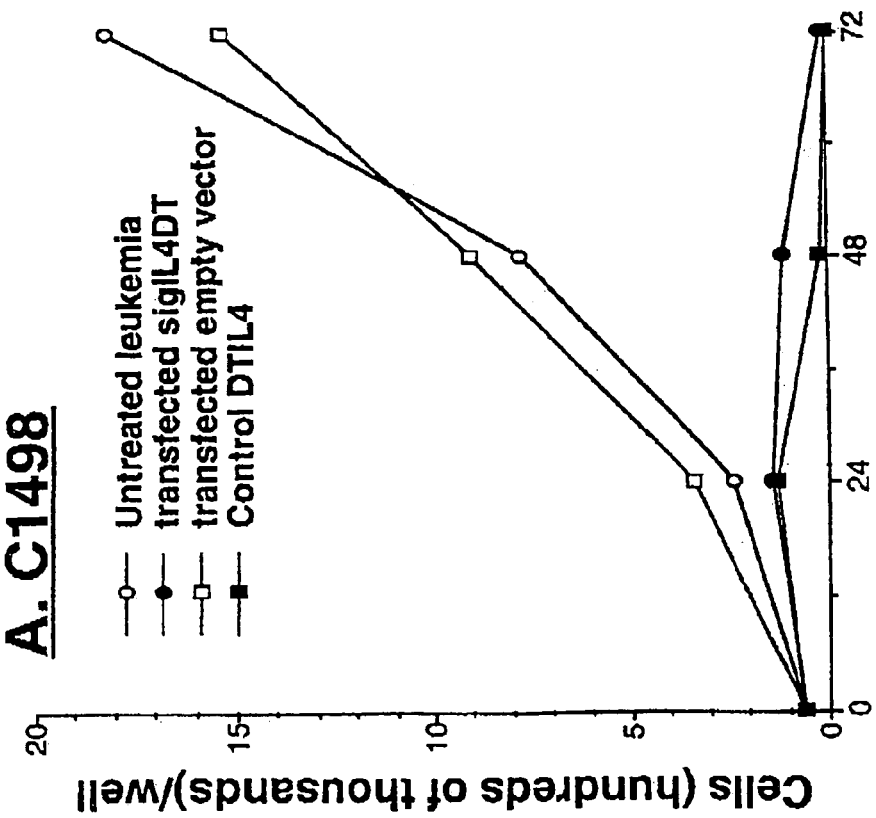
FIG. 3A
FIG. 3B

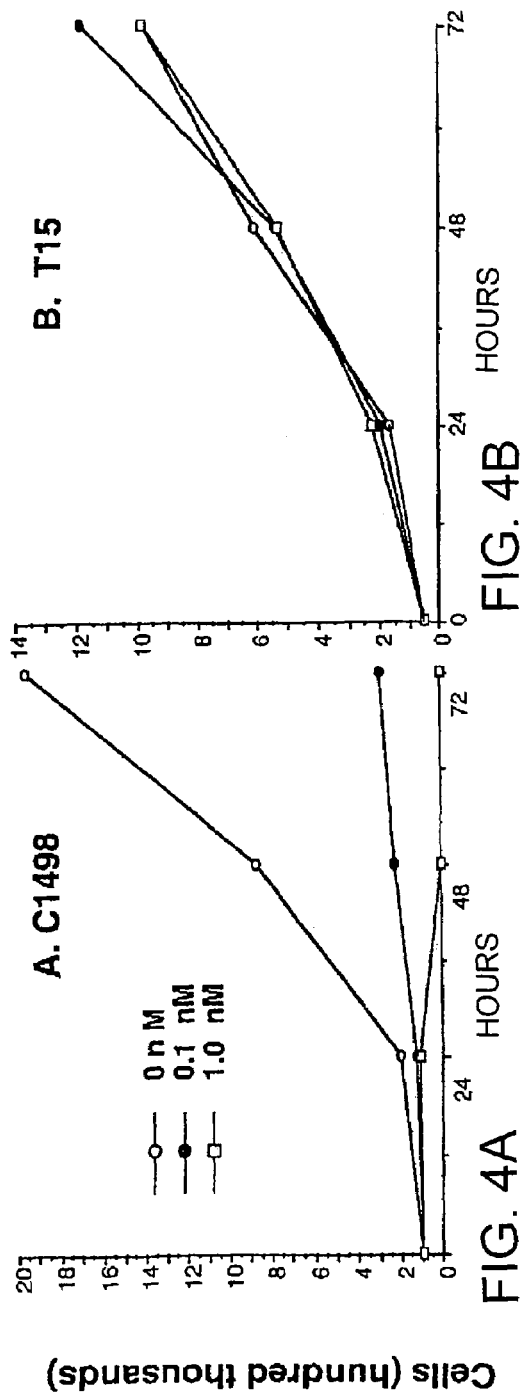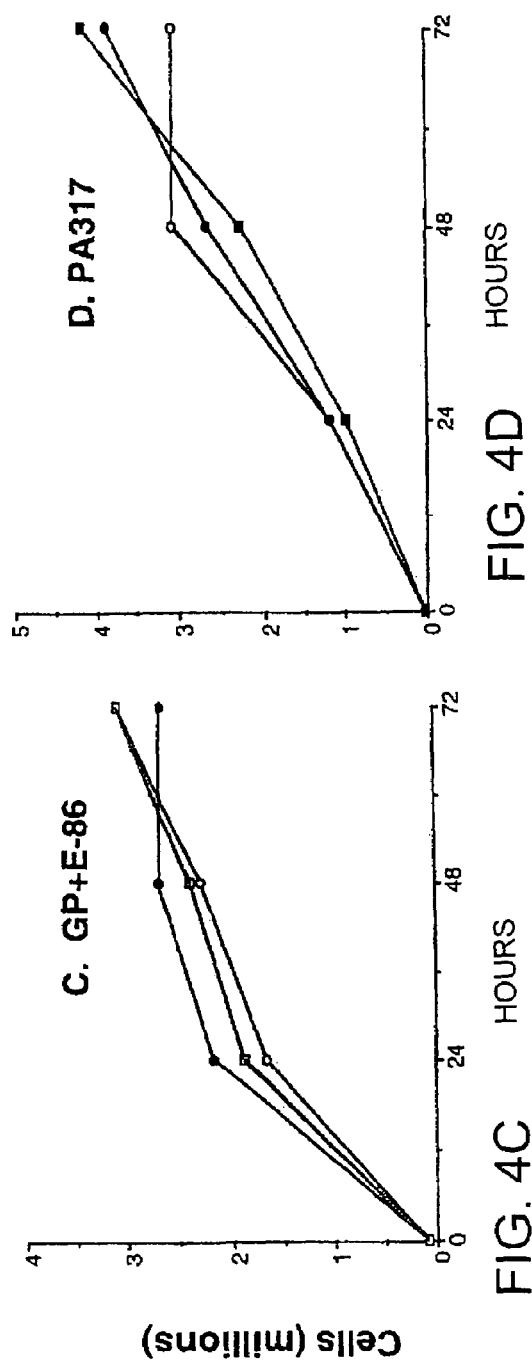
FIG. 4A  FIG. 4B  FIG. 4C  FIG. 4D

US 7,101,542 B1

CELL-MEDIATED TARGETING OF TOXINS TO PATHOGENIC CELLS

This application claims priority of Provisional Application No. 60/136,014 filed May 26, 1999.

BACKGROUND OF THE INVENTION

The invention is generally in the field of immunotoxins, particularly immunotoxins effective against pathogenic cells, e.g., cancer cells.

Immunotoxins are multifunctional (e.g., bifunctional) molecules that contain domains that direct the molecules to target cells of interest (e.g., cancer cells) and toxic domains that kill the target cells. They are thus useful in pathological conditions such as cancer, autoimmune diseases, and certain infectious diseases. The field of immunotoxins has been limited by an inability to escalate the dose of immunotoxin administered to a subject to a level that is therapeutic but not unacceptably toxic.

SUMMARY OF THE INVENTION

The invention is based on the discovery that administration to tumor-bearing animals of tumor-specific CD8+ cytotoxic T lymphocytes (CTL) secreting a recombinant immunotoxic fusion protein results in a decrease in tumor growth in the animals. The invention features vectors encoding immunotoxic fusion proteins, targeting cells transduced or transfected with vectors containing DNA sequences encoding immunotoxic fusion proteins, cell populations containing such targeting cells, methods of making the cell populations, and methods of treatment involving administration to subjects (e.g., cancer patients) of either the vectors themselves or the targeting cells. By delivering the immunotoxins to the site at which they are required, the above-mentioned problem of obtaining sufficiently high levels of the immunotoxins, without systemic toxicity, is obviated.

Specifically, the invention features a targeting cell containing a vector which contains a nucleic acid sequence (e.g., DNA, cDNA, or RNA) encoding a fusion protein. The fusion protein includes: (a) a targeting domain which contains a first member of an affinity pair; and (b) a toxic domain which contains a toxic molecule. The targeting cell has significant binding affinity for a pathogenic cell and expresses and secretes the fusion protein. As used herein, a targeting cell with "significant binding affinity" for a pathogenic cell is a targeting cell that physically interacts with a pathogenic cell in such a manner as to deliver an amount of the immunotoxic fusion protein to the pathogenic cell sufficient to kill the target cell.

The first member of the affinity pair binds to a second member which is expressed on the surface of the pathogenic cell. The first member of the affinity pair can be: a cytokine (e.g., IL-1, IL-2, IL-3, IL-4, IL-5, IL-6, IL-7, IL-8, IL-10, IL-12, IL-13, IL-15, interferon (IFN)-α, IFN-γ, IFN-β, tumor necrosis factor (TNF)-α, a transforming growth factor (TGF) (e.g., TGF-α or TGF-β), granulocyte-macrophage colony stimulating factor (GM-CSF), vascular endothelial growth factor (VEGF), or epidermal growth factor (EGF)); an antigen; a ligand for a cell adhesion receptor; a ligand for a signal transduction receptor; a hormone; and a molecule that binds to a death domain family molecule (e.g., Fas ligand, TRAIL, or TWEAK).

The second member of the affinity pair can be: a cytokine receptor (e.g., a receptor for any of the cytokines listed above); an antibody, a cell adhesion receptor, a signal transduction receptor, a hormone receptor, or a major histocompatibility complex (MHC) molecule-peptide complex. The pathogenic cell targeted by the targeting cell can be: a cancer cell (e.g., a malignant hematological cell such as a leukemia cell or a lymphoma cell); a neural tissue cancer cell, a melanoma cell, a breast cancer cell, a lung cancer cell, a gastrointestinal cancer cell, an ovarian cancer cell, a testicular cancer cell, a lung cancer cell, a prostate cancer cell, a cervical cancer cell, a bladder cancer cell, a vaginal cancer cell, a liver cancer cell, a renal cancer cell, a bone cancer cell, or a vascular tissue cancer cell); a cell (e.g., a CD4+ T lymphocyte, a CD8+ T lymphocyte, a B lymphocyte, a monocyte, or a macrophage) associated with the pathogenesis of an autoimmune disease (e.g., rheumatoid arthritis (RA), insulin-dependent diabetes mellitus (IDDM), multiple sclerosis, systemic lupus erythematosus (SLE) and myasthenia gravis (MG)); a cell that is infected with a microorganism such as a virus (e.g., human immunodeficiency virus or influenza virus), a bacterium, or a protozoan parasite. Where the virus infecting the pathogenic cell is HIV, the first member of the affinity pair can be CD4, CCR4, or CCR5 and the second member can be HIV envelope glycoprotein.

The targeting cell can be a CD8+ T lymphocyte, a CD4+ T lymphocyte, a B lymphocyte, a natural killer (NK) cell, a lymphokine-activated killer (LAK) cell, a monocyte, or a macrophage. The toxic molecule can be diphtheria toxin (DT) (e.g., amino acids 1–390 of DT), ricin, *Pseudomonas* exotoxin (PE), bryodin, gelonin, α-sarcin, aspergillin, restrictocin, angiogenin, saporin, abrin, and pokeweed antiviral protein (PAP). The vector can be a retroviral vector, a plasmid, an adenoviral vector, a adeno-associated viral vector, a vaccinia viral vector, a lentiviral vector, or a herpes viral vector. The vector can contain, 5' of the 5' end of the encoding sequence, a signal sequence, e.g., a signal sequence encoding a natural leader sequence of the first member (e.g., IL-4).

The invention also features a population of cells, a substantial number (e.g., at least 0.001%, at least 0.01%, at least 0.1%, at least 1%, at least 10%, at least 20%, at least 40%, at least 60%, at least 80%, at least 90%, at least 95%, at least 99%, or even 100%) of which are the targeting cell described above.

Another feature of the invention is a vector containing a nucleic acid (e.g., DNA, cDNA, or RNA) sequence encoding a fusion protein. The fusion protein includes: (a) a targeting domain which contains a first member of an affinity pair (e.g., any of those listed above); (b) a toxic domain which contains a toxic molecule (e.g., any of those listed above); and (c) transcriptional and translational regulatory sequences, operably linked to the nucleic acid sequence, which allow for expression of the fusion protein in a cell of a mammal. The first member of the affinity pair binds to a second member (e.g., those listed above) which is expressed on the surface of a pathogenic cell (e.g., those listed above). The vector can contain, 5' of the 5' end of the coding sequence, a signal sequence, e.g., a signal sequence encoding a natural leader sequence of the first member (e.g., IL-4). The vector can be a retroviral vector, a plasmid, an adenoviral vector, a adeno-associated viral vector, a vaccinia viral vector, a lentiviral vector, or a herpes viral vector.

Also encompassed by the invention is a method of treating a subject with a pathogenic cell disease (e.g., any of the malignant and non-malignant diseases listed above) involving administering the above cell population to the subject. An alternative method of treatment involves administering the above-described vector to the subject.

Another embodiment of the invention is a method of making the above described cell population. The method involves: (a) providing a cell preparation wherein each of a substantial number (e.g., at least 0.001%, at least 0.01%, at least 0.1%, at least 1%, at least 10%, at least 20%, at least 40%, at least 60%, at least 80%, at least 90%, at least 95%, at least 99%, or even 100%) of the cells (e.g., the targeting cell-types listed above) of the preparation has significant binding affinity for a pathogenic cell (e.g., those listed above); and (b) transfecting or transducing the cells of the preparation with the above-described vector. After the transfection or transduction, a significant number (e.g., at least 0.001%, at least 0.01%, at least 0.1%, at least 1%, at least 10%, at least 20%, at least 40%, at least 60%, at least 80%, at least 90%, at least 95%, at least 99%, or even 100%) of the cells of the preparation express and secrete the fusion protein. The method can include, after transfection or transduction, enriching for cells (e.g., by limiting dilution cloning, fluorescence activated cell sorting (FACS), or selection with a selectable marker encoded by a gene in the vector, e.g., the Neo gene) expressing and secreting the fusion protein.

As used herein, an "affinity pair" is any pair of polypeptide molecules that have an intrinsic ability to bind to each other. Thus, affinity pairs include, without limitation, any receptor-ligand pair, e.g., cytokines/cytokine receptors, hormones/hormone receptors, signal transduction ligands/signal transduction receptors, adhesion ligands/adhesion receptors, death domain molecule binding ligands/death domain molecules, and antigens/antibodies. Not included in the invention are those affinity pairs in which the member of the pair contained in the fusion protein (i.e., the "first member") is an antibody molecule, or a fragment of an antibody molecule, that binds to a molecule on the surface of a pathogenic cell.

As used herein, a "pathogenic cell" is a cell that is associated with the signs, symptoms, or causes of a disease or disorder in a subject. Thus, a pathogenic cell can be a cancer cell, a cell associated with the symptoms of an autoimmune disease, or a cell that harbors an infectious microorganism.

It is understood that all polypeptides listed for use as targeting domains, toxic domains, or signal peptides include functional fragments of such polypeptides. A functional fragment of a polypeptide is a fragment that is shorter than the full-length polypeptide. Functional fragments of toxic polypeptides kill target cells with at least 20%, at least 40%, at least 60%, at least 80%, at least 90%, or 100% (or higher), of the efficiency of the parent polypeptide. Functional fragments of targeting polypeptides (i.e., first members of affinity pairs) bind to relevant second members of the affinity pairs with at least 20%, at least 40%, at least 60%, at least 80%, at least 90%, or 100% (or higher) of the avidity of the parent polypeptide. Functional fragments of signal peptides are those fragments that direct the polypeptide with which the signal peptide fragments are associated to the lumen of the endoplasmic reticulum during translation with at least 20%, at least 40%, at least 60%, at least 80%, at least 90%, or 100% (or higher) of the efficiency of the parent signal peptide. Methods of comparing the cytotoxic activity, the binding avidity, and the ability to enter the endoplasmic reticulum during translation, of different polypeptides are known in the art. In addition, targeting polypeptides, toxic polypeptides, and signal polypeptides can contain conservative substitutions. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. In addition, the materials, methods, and examples are illustrative only and not intended to be limiting.

Other features and advantages of the invention, e.g., methods of treating cancer, will be apparent from the following description, from the drawings and from the claims.

BRIEF DESCRIPTION OF THE DRAWINGS

FIG. 1A is a diagram of a plasmid which was used to produce the DT390IL-4 fusion protein in E. coli bacteria. FIG. 1B is a diagram of a plasmid used to express the sigIL-4DT390 fusion protein in fibroblasts. FIG. 1C is a diagram of a retroviral vector used to express the sigIL-4DT390 fusion protein in fibroblasts, T15 cells, and LAK cells. FIG. 1D is a diagram of the same vector shown in FIG. 1C, except that the Neo gene is replaced with a nerve growth factor receptor (NGFR) gene.

FIG. 2A is a line graph showing the toxic effect of DT390IL-4 fusion protein on the viability of C1498 tumor cells. FIGS. 2B and 2C are line graphs showing the results of blocking assays performed in the presence of DT390IL-4 fusion protein and either anti-IL-4 antibody (FIG. 2C) or an irrelevant control antibody (anti-Ly5.2) (FIG. 2B).

FIGS. 3A and 3B are line graphs showing the effect of sigIL-4DT390 fusion protein on the viability of IL-4R expressing C1498 tumor cells (FIG. 3A) and IL-4R non-expressing EL-4 tumor cells (FIG. 3B).

FIGS. 4A–4D are line graphs showing the effect of DT390IL-4 fusion protein on the viability of IL-4R+ C1498 cells (FIG. 4A), IL-4R– T15 cells (FIG. 4B), IL-4R– GP+E-86 packaging cells (FIG. 4C), and IL-4R– PA317 packaging cells (FIG. 4D).

DETAILED DESCRIPTION

Figures 1A, 1B, 1C, 1D:
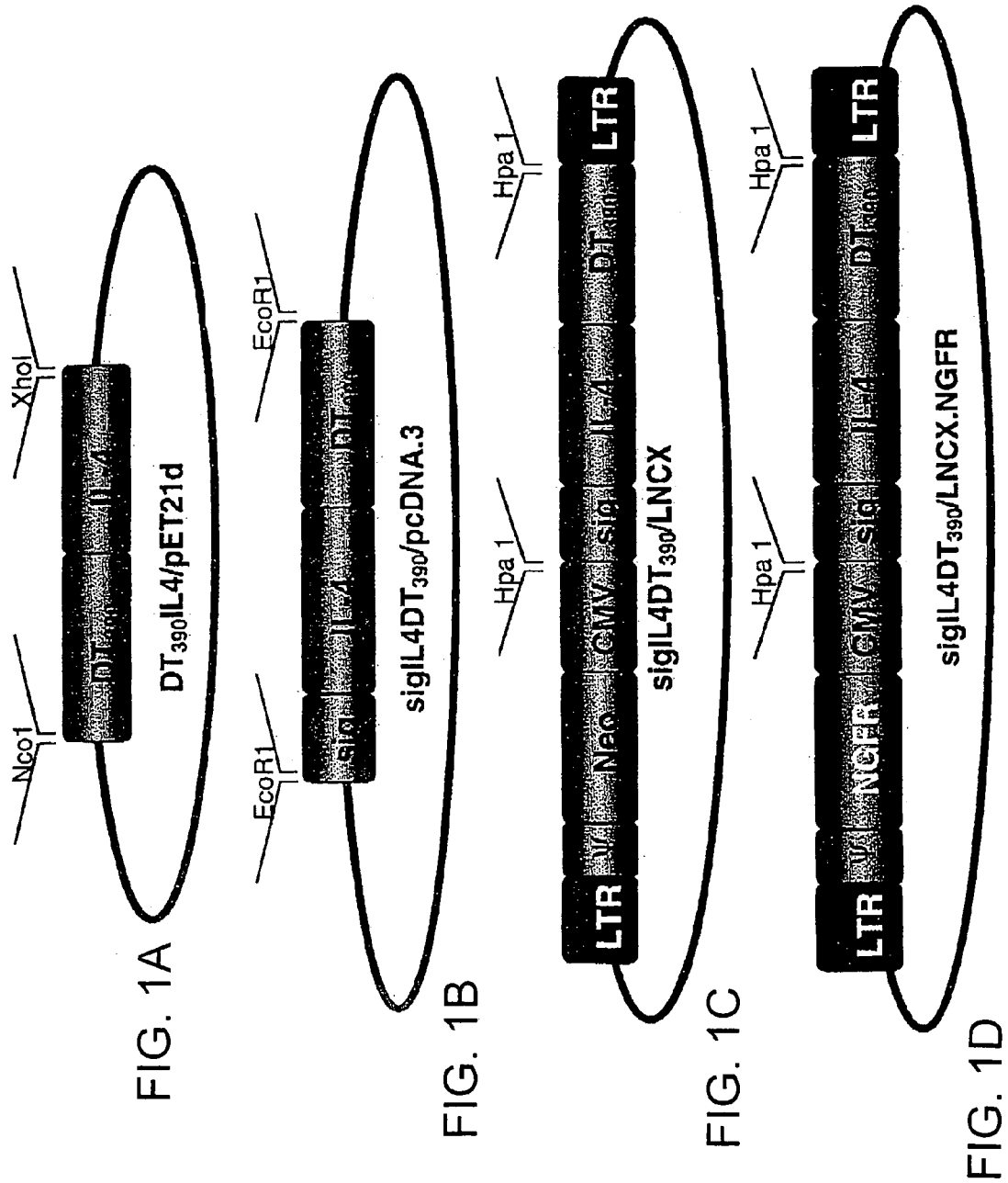
FIGS. 1A–1D are diagrams of expression vectors used to induce expression of immunotoxic fusion proteins containing IL-4 and DT390 toxic domains.
Figure 5:
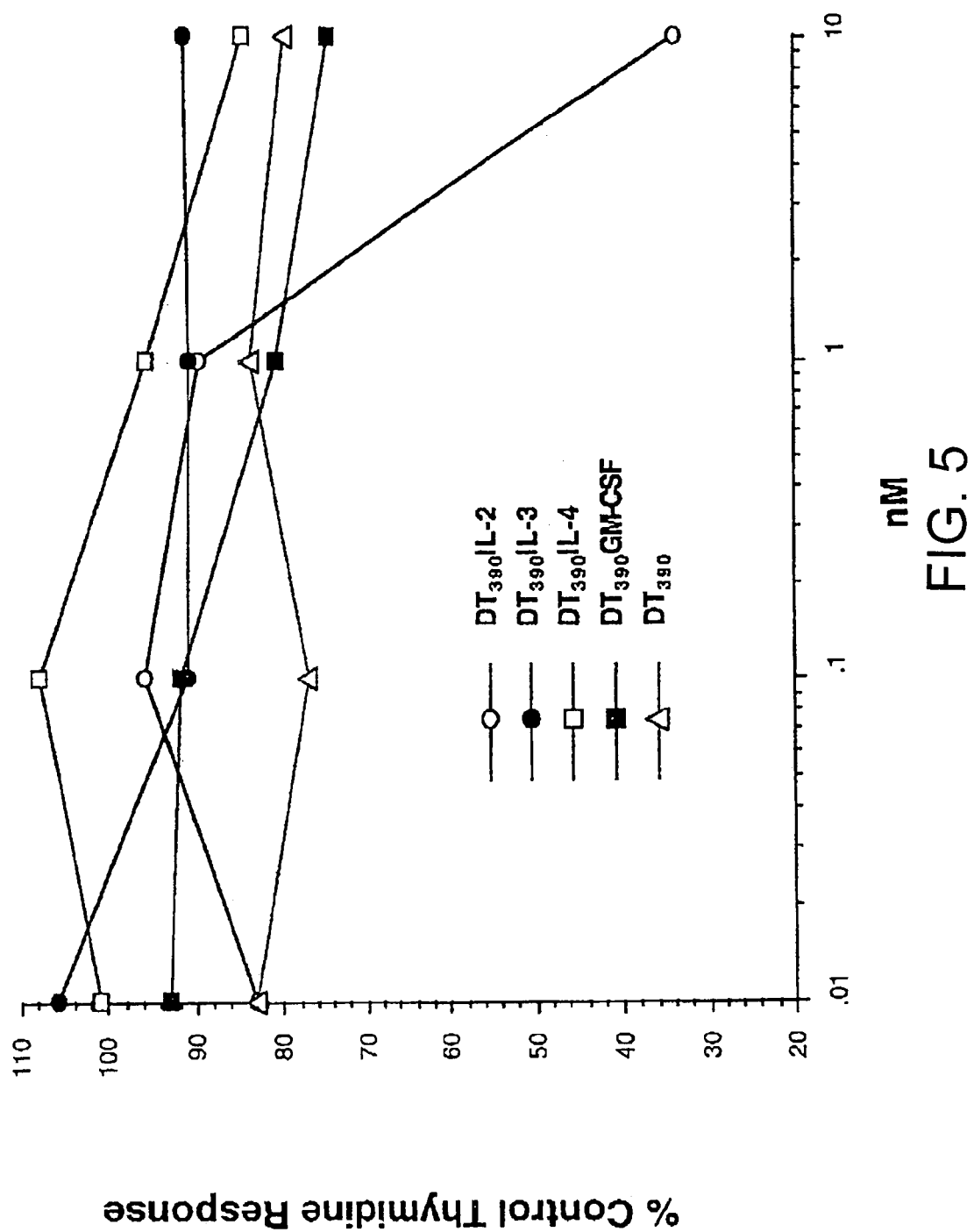
FIG. 5 is a line graph showing the effect of DT390IL-2, DT390IL-3, DT390IL-4, DT390GM-CSF, and DT390 on the proliferation of IL-4R–, IL-2R+ T15 cells.
Figure 6:
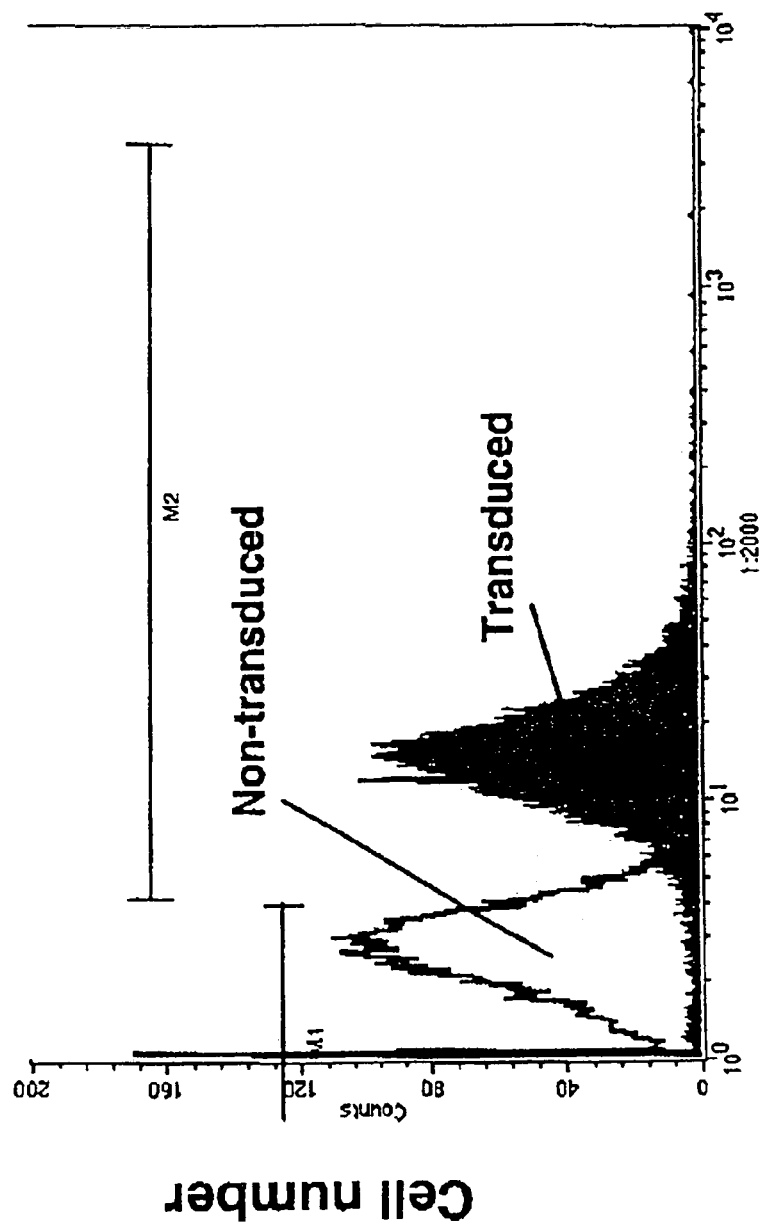
FIG. 6 is fluorescence flow cytometric (FFC) profile of T15 cells transduced with the retroviral vector (containing the nucleic acid sequence encoding sigIL-4DT390) shown in FIG. 1D and stained for cell surface expression of NGFR.
Figures 7A, 7B:
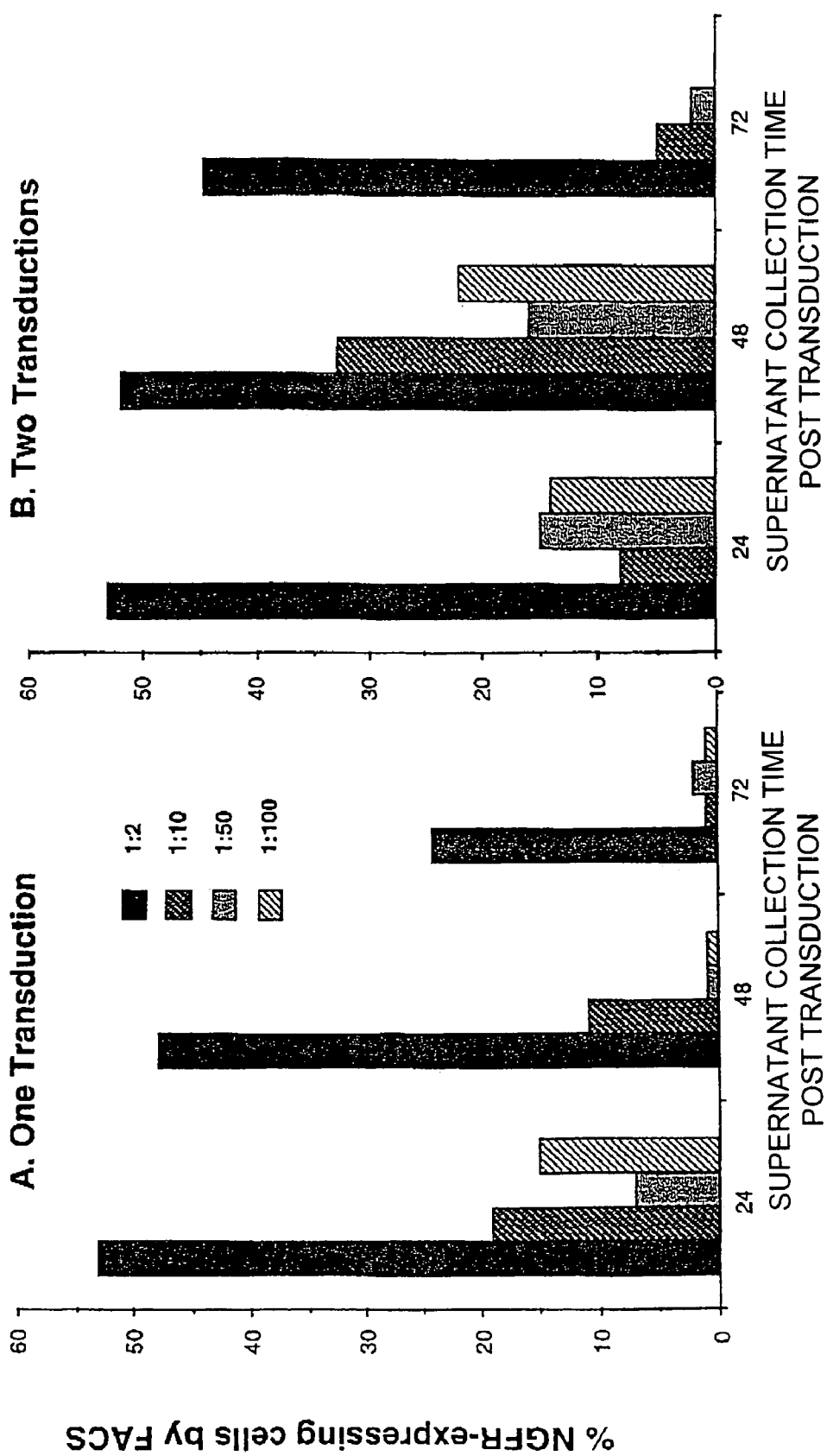
FIGS. 7A and 7B are bar graphs showing the efficiency of transduction of T15 cells after one (FIG. 7A) and two (FIG. 7B) transductions with the vector shown in FIG. 1D.
Figure 8:
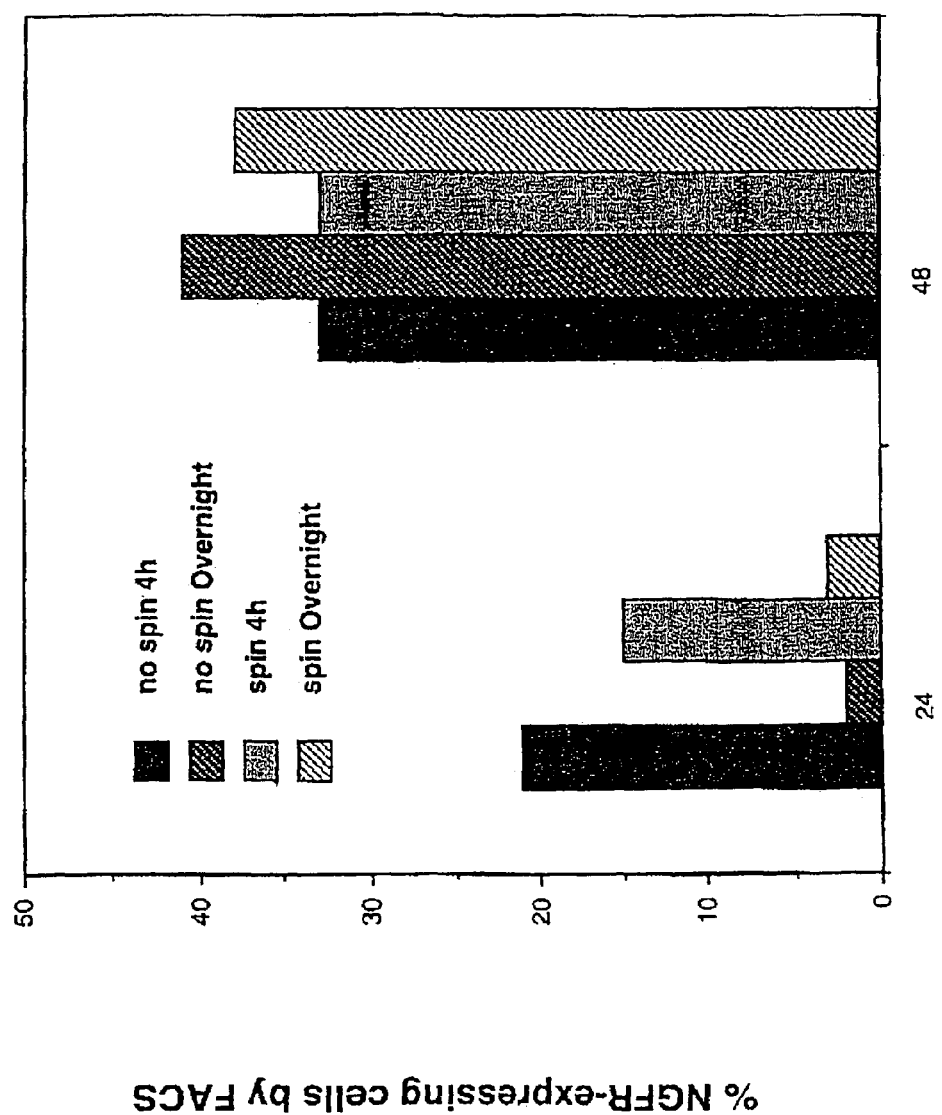
FIG. 8 is a bar graph showing the relative efficiency of transduction of T15 cells with the vector shown in FIG. 1D using spin transduction and transduction without spinning.
Figure 9:
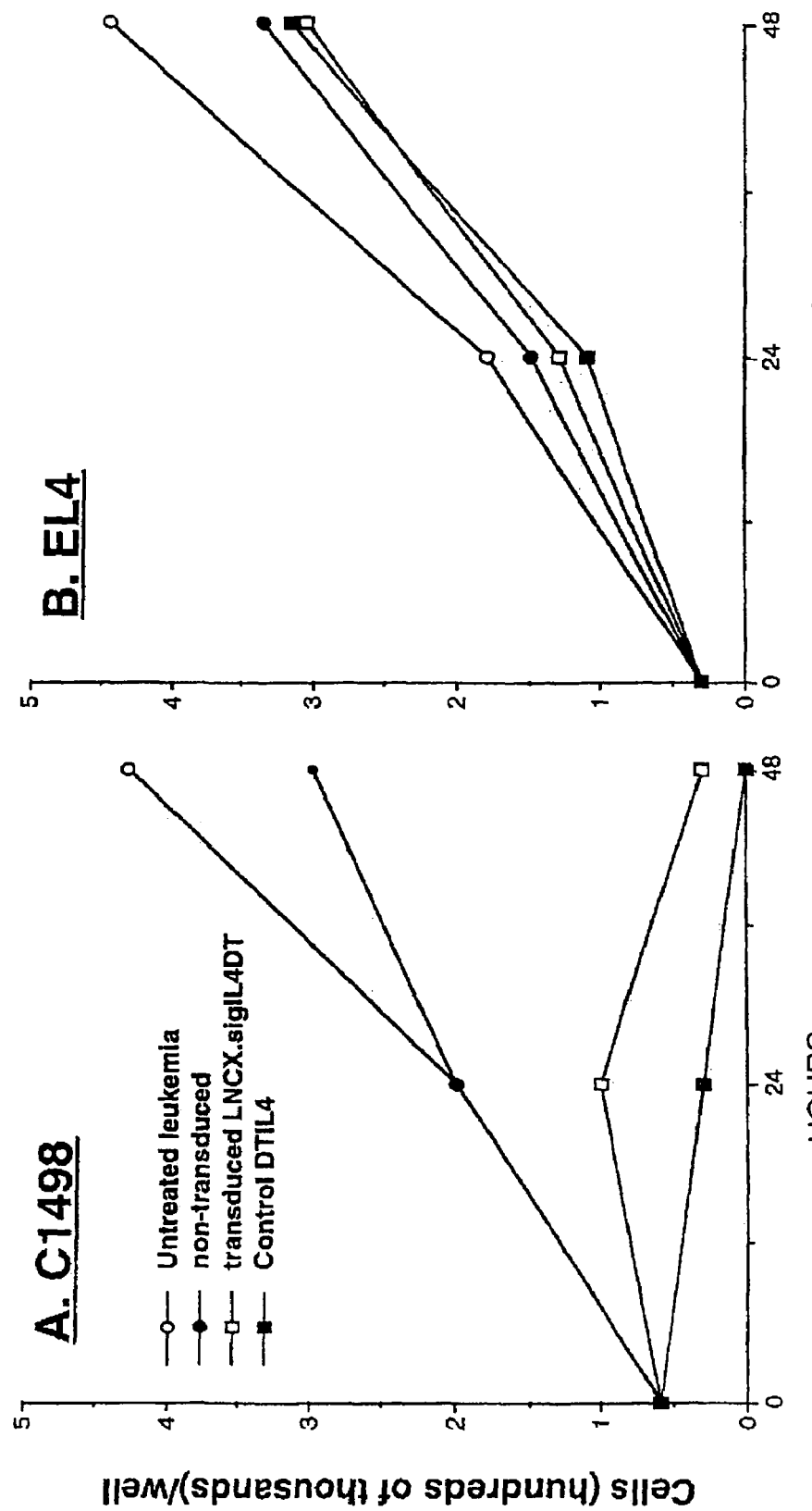
FIG. 9A and FIG. 9B are line graphs showing the effect of sigIL-4DT390 fusion protein on the viability of IL-4R+ C1498 tumor cells (FIG. 9A) and IL-4R– EL-4 tumor cells (FIG. 9B).
Figure 10:
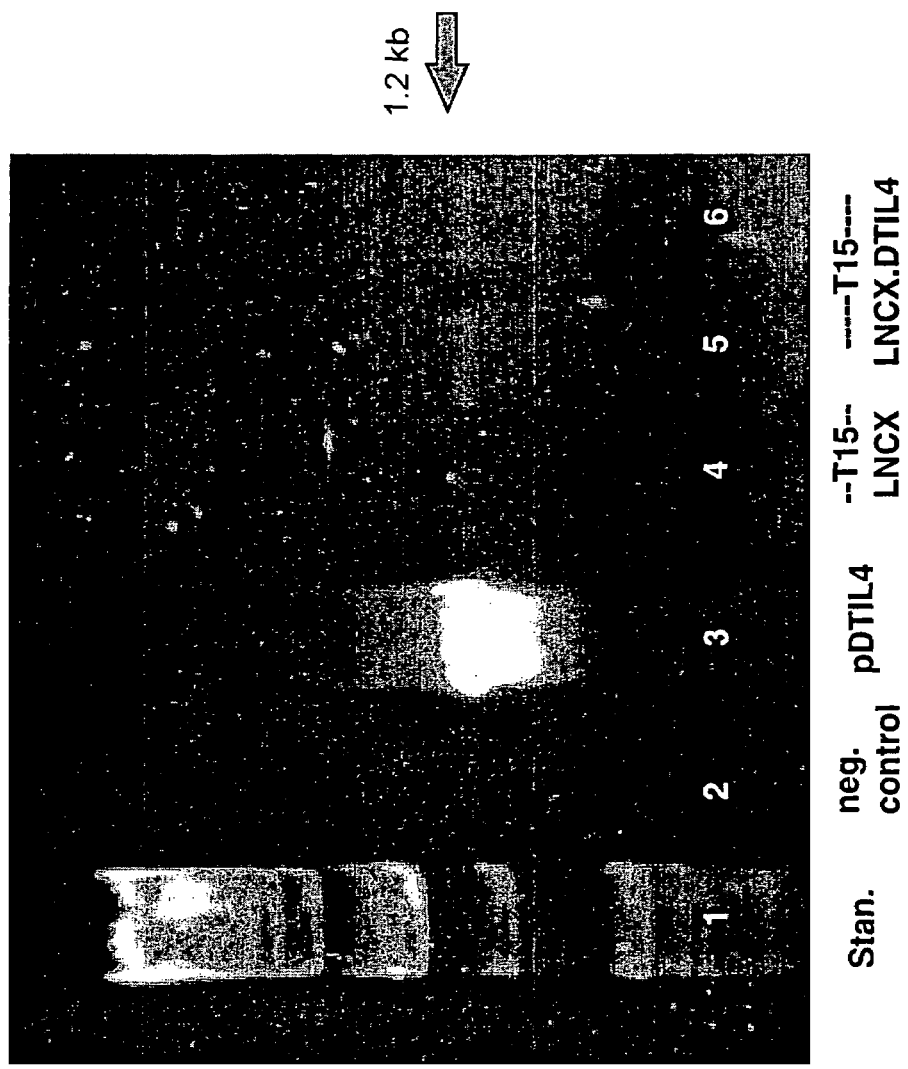
FIG. 10 is a photograph of an ethidium bromide stained agarose electrophoresis gel of PCRs using DT specific oligonucleotide primers and the following templates: DNA extracted from T15 cells two weeks after transduction with the vector shown in FIG. 1C (lanes 5 and 6); DNA from control T15 cells transduced with a retroviral vector not containing a coding sequence (lane 4); the vector shown in FIG. 1A (lane 3); and no template (lane 2). Lane 1 contains molecular size markers (HindIII digested phage λ DNA).
Figure 11:
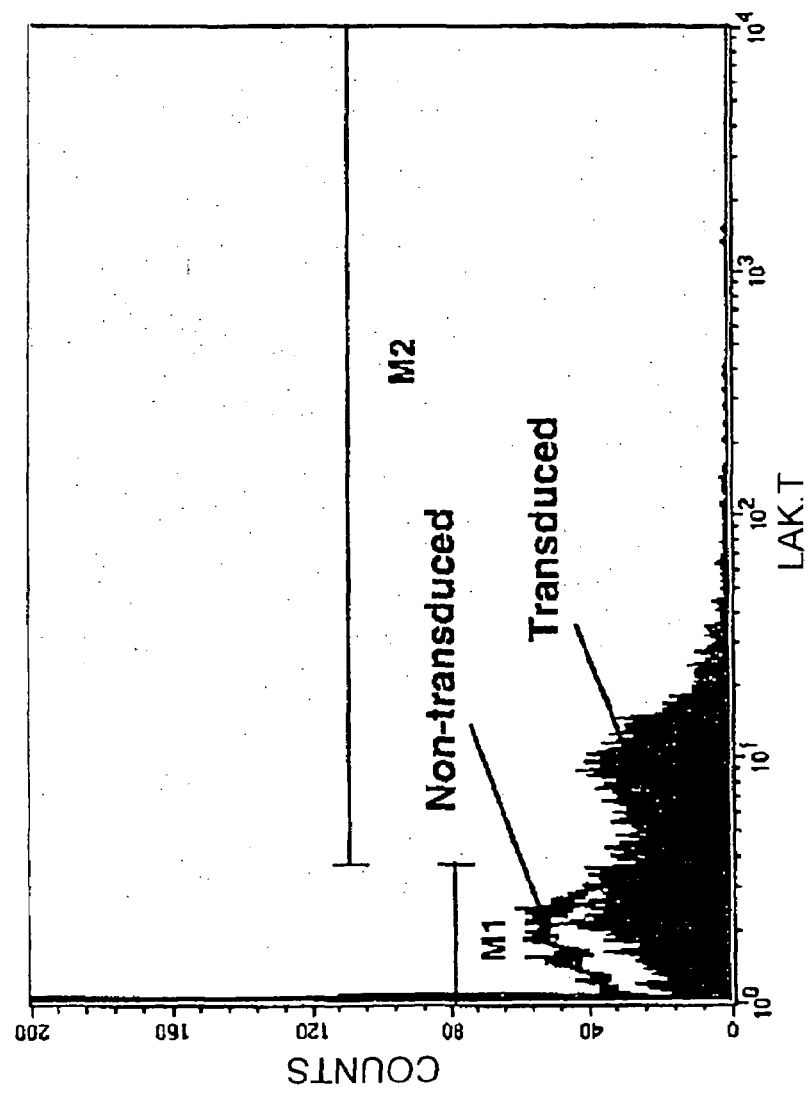
FIG. 11 is a FFC profile of LAK cells transduced with the vector shown in FIG. 1D and stained for cell surface expression of NGFR. The profile indicates a transduction frequency of about 20%.
Figure 12:
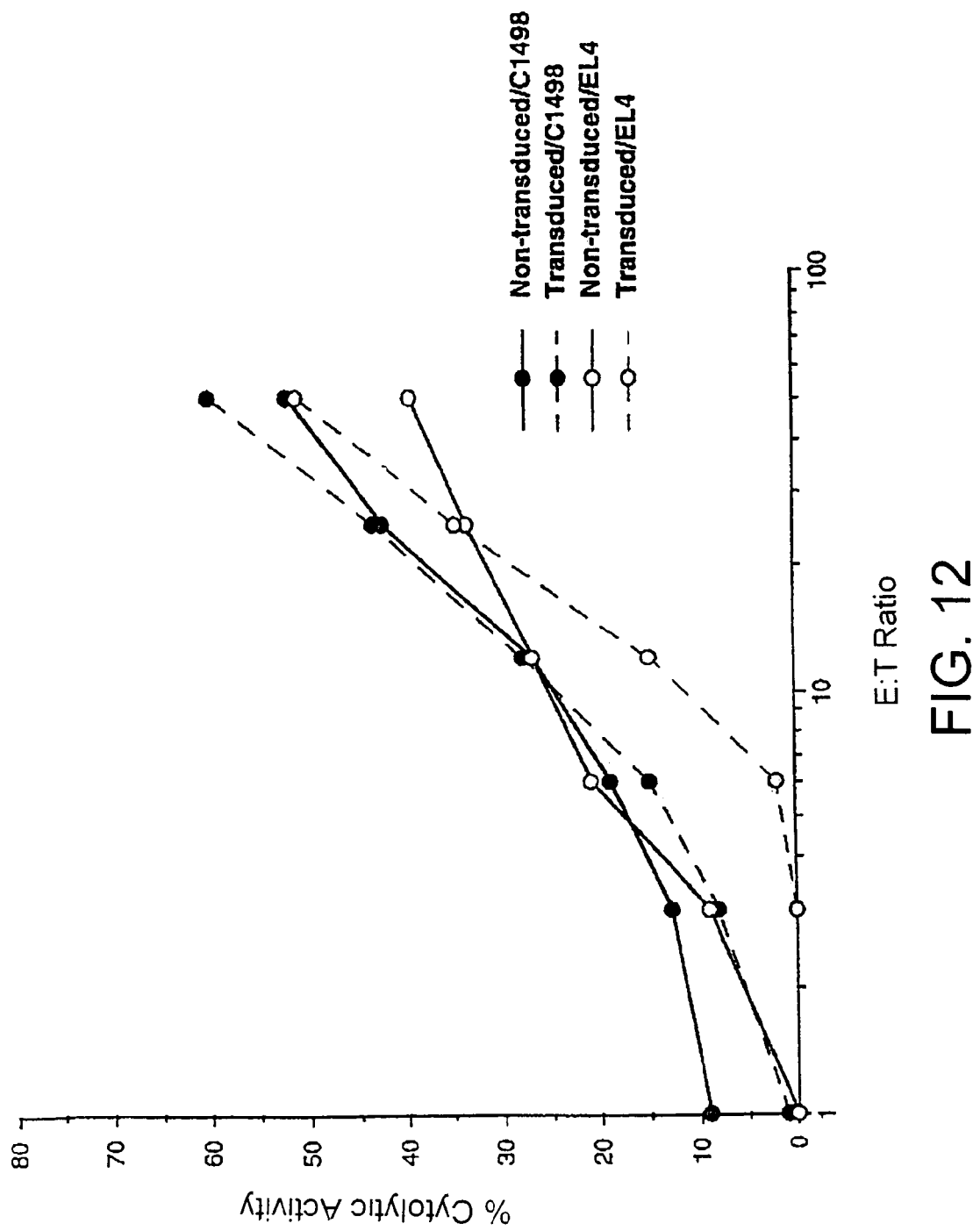
FIG. 12 is a line graph showing the ability of LAK cells, either untransduced or transduced with the vector shown in FIG. 1D, to kill C1498 and EL-4 tumor cells in short term cytotoxicity assays.
Figure 13:
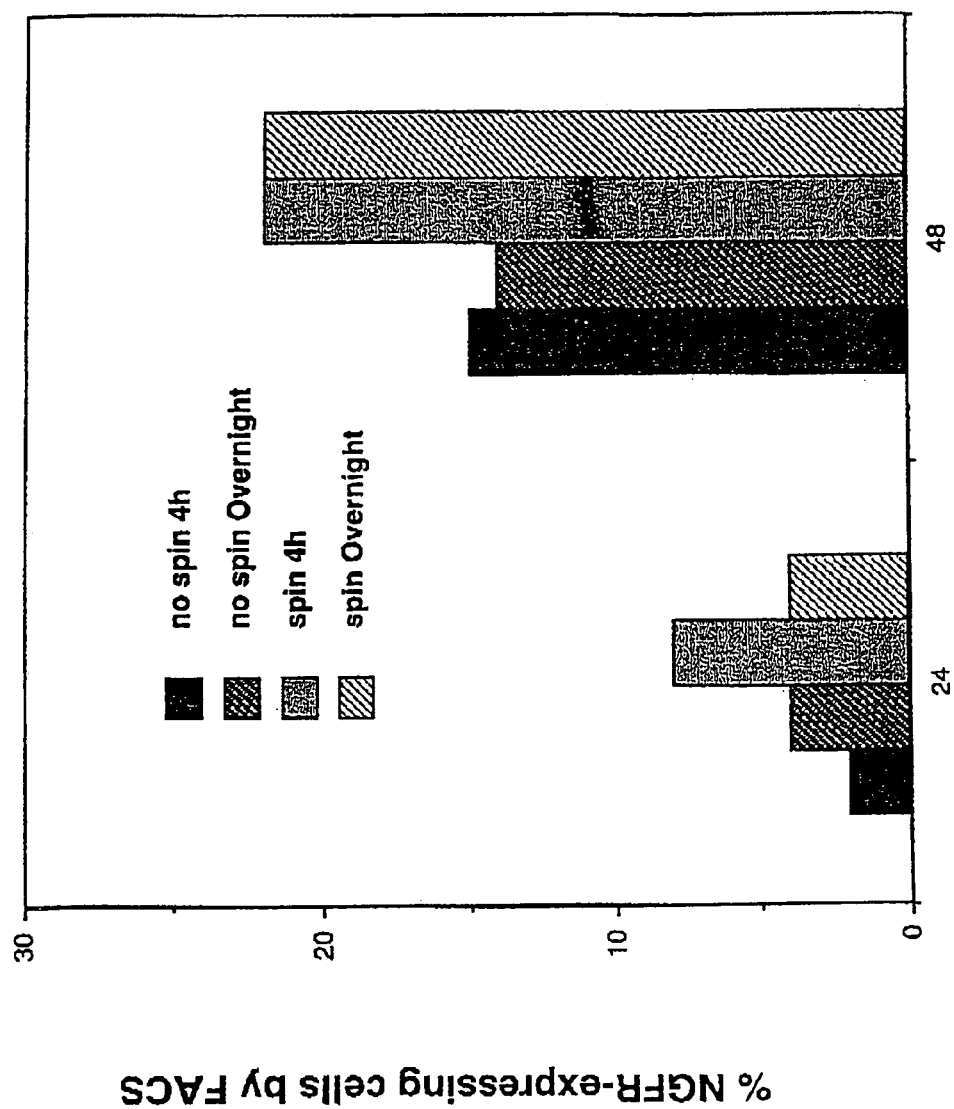
FIG. 13 is a bar graph showing the relative efficiency of transduction of LAK cells with the vector shown in FIG. 1D using spin transduction and transduction without spinning.
Figures 14A, 14B:
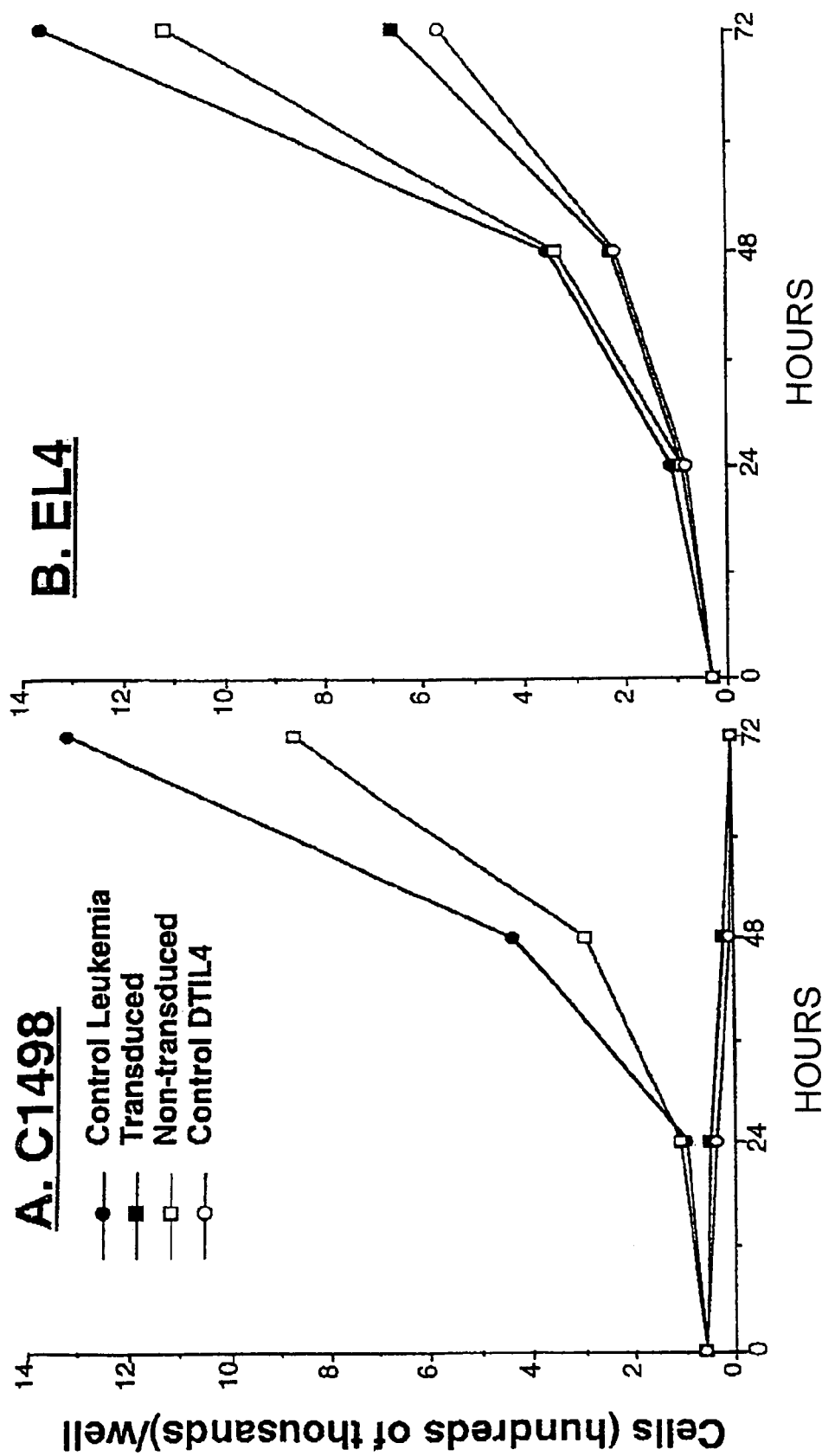
FIG. 14A and FIG. 14B are line graphs showing the effect on the viability of IL-4R+ C1498 tumor cells (FIG. 14A) and IL-4R− EL-4 tumor cells of culture supernatant derived from non-transduced LAK cells, culture supernatant from LAK cells transduced with the vector shown in FIG. 1C, no culture supernatant ("control leukemia"), and DT390IL-4 fusion protein.
Figure 15:
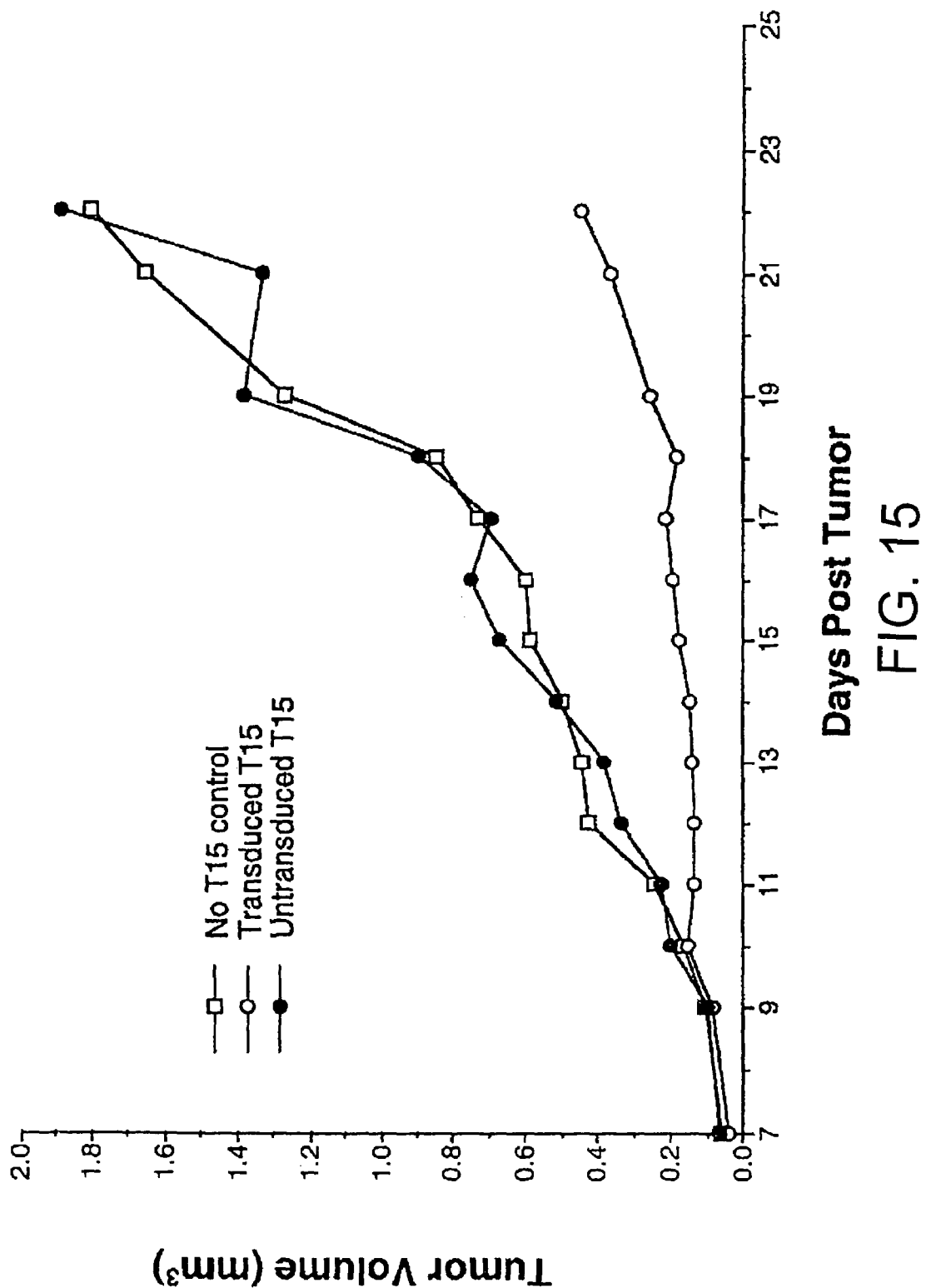
FIG. 15 is a line graph showing the effect, in vivo, of C1498 tumor growth in mice injected with nothing, untransduced tumor cells, or T15 cells transduced with the vector shown in FIG. 1C.
Figure 16:
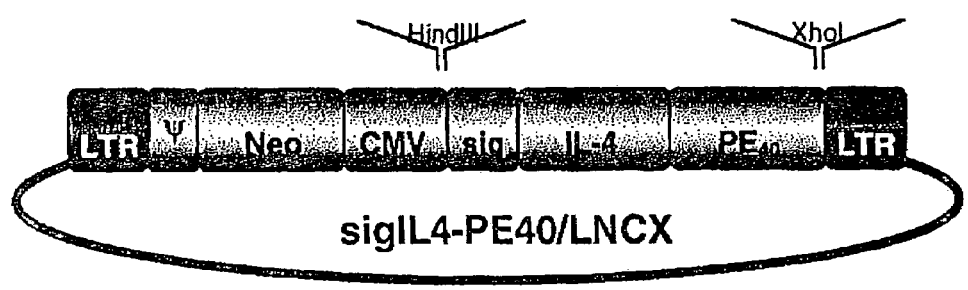
FIG. 16 is a diagram of a retroviral vector used to express the sigIL-4PE40 fusion protein in fibroblasts.

The invention is based on a series of experiments demonstrating that a cell (e.g., a tumor-specific CTL) with specific binding affinity for a particular target cell (e.g., a tumor cell) could act as an efficient delivery vehicle for an immunotoxic fusion protein with the ability to bind to the target cell and then kill it.

A fusion protein (DT390IL-4) containing the toxic domain (DT390) of diphtheria toxin (DT) and the IL-4 polypeptide killed IL-4 receptor (IL-4R) bearing C1498 tumor cells but not tumor cells that did not express the IL-4R. Transfection of fibroblasts with an expression vector containing a construct that encoded a fusion protein (sigIL-4DT390) composed of the native IL-4 signal peptide, the mature IL-4 protein, and DT390, resulted in intracellular expression and secretion of the fusion protein.

Experiments involving testing of the relevant cells for susceptibility to the toxic effects of DT390IL-4 indicated that a CD8+ CTL line (T15) specific for C1498 tumor cells was suitable for transduction with vectors containing constructs encoding fusion proteins with DT390 and IL-4 domains. In addition, two fibroblast packaging cell lines were suitable for making vectors containing such constructs. Both T15 cells and LAK cells were effectively transduced by the sigIL-4DT390 expressing retroviral vector and secreted sufficient amounts of the fusion protein to kill C1498 cells in an in vitro assay. A similar retroviral construct in which the DT390 encoding DNA sequence was replaced with a DNA sequence encoding a toxic fragment of Pseudomonas exotoxin efficiently transduced fibroblasts and the relevant toxic fusion protein was expressed intracellularly by the transduced fibroblasts. Administration of T15 cells transduced with the sigIL-4DT390 encoding vector to mice that had been injected with C1498 tumor cells resulted in decreased growth of the tumor cells.

These experiments indicated that cells with significant binding affinity for relevant target cells can be used to effectively deliver immunotoxic fusion proteins to such target cells. Thus, such targeting cells, after transduction or transfection with vectors encoding immunotoxic fusion proteins, can be used to treat a wide range of diseases involving pathogenic cells.

A. Targeting Cells

Any cell that has significant binding affinity for a target cell of interest, and which is itself not susceptible to the toxic effects of the relevant immunotoxic fusion protein, can be used as a targeting cell. The targeting cell preferably should not express a high level of receptors that bind targeting domain of the fusion protein. More preferably, the targeting cells should express no such receptors. Thus, for example, T cells (CD8+ or CD4+) or B cells with cell surface antigen-specific receptors specific for an antigen expressed on the surface of a target cell of interest can be used as targeting cells for targeting fusion proteins containing targeting domains for which the T or B cells have either no or low levels of a binding receptor. T and B cells are suitable for use as targeting cells in which it is desired to kill: (a) tumor cells expressing cell surface antigens recognizable by antigen-specific receptors on the B cells or expressing peptide-major histocompatibility complex (MHC) molecule (class I or class II) complexes recognizable by antigen specific T cell receptors (TCR) on the T cells; (b) cells infected with an intracellular infectious microorganism (e.g., a bacterium, a virus, or a protozoan parasite) and thus expressing on their surface either antigens, produced or induced by the microorganism, and recognizable by B cell receptors or peptide fragments of proteins, produced by or induced by the microorganism, bound to MHC class I or MHC class II molecules on the surface of the target cell and thus recognizable by TCR on the T cells. LAK cells and natural killer (NK) cells, which have the ability to bind to a wide range of tumor target cells, are also appropriate for use as targeting cells with tumor target cells. Targeting cells with cytotoxic activity (e.g., CTL, NK cells, and LAK cells) have the advantage of acting additively or, preferably, synergistically with the immunotoxins to kill relevant target cells.

The targeting cells can be freshly obtained from a subject. The cells of interest (e.g., CD8+ T cells) can be enriched or purified from mixed populations (e.g., lymph nodes, spleen, cord blood, or peripheral blood mononuclear cells (PBMC)) by methods known in the art. Where lymphocytes are used as targeting cells, the subject from which they are obtained will preferably have been exposed to an antigen expressed by the target cell (e.g., a tumor cell or an infected cell) of interest. In this way the population obtained from the subject will be enriched for lymphocytes expressing cell-surface receptors specific for the antigen of interest. Tumor infiltrating lymphocytes (TIL), which are T cells isolated from the tumor of subject, can be a useful source of tumor-specific T cells.

The targeting cells can be enriched for such receptor bearing cells in vitro. Thus, for example, T lymphocytes can be cultured in the presence of an isolated antigen itself (e.g., an isolated tumor associated antigen or infectious microorganism antigen), or an antigenic peptide fragment of such an antigen, and appropriate antigen presenting cells (APC) (e.g., B cells, dendritic cells, macrophages, or monocytes). Alternatively, the T cells can be cultured with cells expressing the antigen, e.g., tumor cells or microorganism (e.g., virus) infected cells. The lymphocyte cultures can be supplemented with one or more growth and/or differentiative factors such as interleukin (IL)-2, IL-4, IL-5, IL-6, IL-12, or interferon-γ (IFN-γ). In addition, the lymphocyte cultures can be multiply restimulated with APC and isolated antigen or antigen expressing cells (e.g., tumor cells or microorganism infected cells). The restimulations can be performed once weekly, once every 10 days, once every two weeks, once every two weeks, once every three weeks, or once a month and can include supplementation with one or more of the above growth or differentiative factors. Furthermore, instead of using isolated antigen (or antigenic peptide), tumor cells, or infected cells as sources of antigen for the cultures, cell lines transfected with or transduced with vectors containing nucleic acid sequences encoding the antigens or antigenic peptides can be used as a source of APC expressing the relevant antigen or antigenic peptide. Where CD8+ T cells are being activated, the transfected or transduced cells will generally express MHC class I molecules and where CD4+ T cells are being activated they will generally express MHC class II molecules. In primary as well as restimulation cultures, the APC or transfected/transduced cell lines used for T cell activation can, optionally, prior to addition to the cultures, be rendered non-proliferative by treatment with agents known in the art (e.g., ionizing radiation or mitomycin-C). The more often the T cell cultures are restimulated, the greater will be the proportion of T cells with specificity for and thus significant binding affinity for the relevant peptide-MHC molecule complex expressed on the surface of the target cell of interest. In a preferred embodiment, the targeting cells will be clonal. Methods of cloning dividing cells (e.g., activated T lymphocytes) are known in the art.

While the above description focuses on cells of the immune system for use as targeting cells, since cells of particular histological type home to tissues or organs containing cells with which they naturally interact (i.e., target cells), it is understood that many other cell types can be used. Thus, for example, cells of neurological origin (e.g., a neuron) or hematopoietic origin (e.g. macrophages, monocytes, or granulocytes, and hematopoietic stem cells such as bone marrow stem cells) can be used as targeting cells. In addition, the targeting cells of the invention do not necessarily need to bind to the target cells themselves. It is only necessary that they interact with a cell in the vicinity of the target cell. Thus, for example, in insulin-dependent diabetes mellitus (IDDM) and rheumatoid arthritis (RA), in which the pathogenic (target) cells are, for example, CD4+ T cells, a targeting cell could be a pancreatic cell and a synovial cell, respectively, which home to pancreas and to joints, respectively. However, the fusion protein secreted by the targeting cells would, in both cases, be one that targets CD4+ T cells. Such a fusion protein could contain as a targeting domain a molecule that binds, for example, to the CD4 molecule, e.g., a MHC class II molecule or a subregion of a MHC class II molecule that binds to CD4.

Targeting cells will generally be histocompatible (i.e., MHC identical) with the subject to which they are to be administered. In a preferred embodiment, they will be autologous, i.e., they will have been derived from the subject or from a monozygotic twin. However, targeting cells can be derived from a donor that is incompatible (at 1 or more (e.g., 2, 3, 4, or 5), or even all MHC class I and/or MHC class II loci) with the recipient. This is because, in some embodiments, it is anticipated that recipients will only require one administration of cells and thus immunological rejection of a subsequent inoculum due to immunization by the first inoculum would not be a complication. In addition, in some embodiments, the targeting cells are expected to be relatively fast acting and will achieve their therapeutic purpose before being rejected by prior activated T cells or antibodies. Furthermore, it is anticipated that some recipients will be relatively immunodeficient due, for example, to chemotherapy, radiotherapy or infection with HIV. Rejection of histoincompatible targeting cells in such patients will be relatively inefficient and slow compared to normal, fully immunocompetent recipients.

Methods of testing a given cell type for its ability to home to a particular organ, tissue, or tumor are known in the art, as are methods for establishing whether a candidate targeting cell is susceptible to the toxic effects of an immunotoxin of interest (e.g., see Example 4).

B. Genetic Constructs

The targeting cells of the invention are genetically engineered to express and secrete an immunotoxic fusion protein of interest. They can be transfected or transduced with either: (a) a single expression vector containing a nucleic acid sequence (e.g., a genomic DNA sequence, a cDNA sequence, or an RNA sequence) encoding a targeting domain fused in frame to a nucleic acid sequence encoding a toxic domain; (b) two vectors each containing the two coding sequences referred to in (a); or (c) a single vector containing the two coding sequences unfused and thus separately transcribed and/or translated. In cases (b) and (c), the polypeptides encoded by the two coding regions are designed so that they associate posttranslationally within the target cell by either covalent (e.g., disulfide) bonds or non-covalent (e.g., hydrophobic or ionic) interactions.

Where a single fusion protein is encoded, the nucleic acid sequence encoding the targeting domain can be 5' of that encoding the toxic domain or vice versa. The two coding sequences will be in frame with each other and can be immediately adjacent to each other or separated by a linker region encoding a linker peptide which can serve, for example, to prevent steric inhibition by the toxic domain of binding of the targeting domain to the surface of the target cell. Linker peptides can be 1 to about 30, even 50, amino acids long and can contain any amino acids. In general, a relatively large proportion (e.g., 20%, 40%, 60%, 80%, 90%, or 100%) of the amino acid residues in the linker will be glycine and/or serine residues.

In a preferred embodiment, the genetic constructs contain a leader sequence that encodes a hydrophobic signal peptide. The leader sequence is at the 5' end of the sequence encoding the fusion protein. The signal peptide is generally immediately N-terminal of the mature polypeptide (fusion protein) but can be separated from it by one or more (e.g., 2, 3, 4, 6, 8, 10, 15 or 20) amino acids, provided that the leader sequence is in frame with the nucleic acid sequence encoding the fusion protein. The signal peptide, which is generally cleaved from the fusion protein prior to secretion, directs fusion proteins into the lumen of the targeting cell endoplasmic reticulum (ER) during translation and the fusion proteins are then secreted, via secretory vesicles, into the environment of the targeting cell. In this way, the targeting cells remain viable since interaction of the toxin with the protein synthetic machinery in the cytosol of the targeting cell is prevented by the membrane bilayers of the ER and secretory vesicles. Useful leader peptides can be the native leader peptide of the relevant targeting domain (e.g., IL-4) or a functional fragment of the native leader. Alternatively, the leader can be that of another exported polypeptide. For example, the signal peptide can have the amino acid sequence MAISGVPVLGFFIIAVLMSAQESWA (SEQ ID NO:1). In addition, the peptide sequence KDEL (SEQ ID NO:2) has been shown to act as a retention signal for the ER.

B.1 Targeting Domains

The targeting domains of the immunotoxic fusion proteins encoded by nucleic acid sequences contained within the vectors of the invention can be any polypeptide (or a functional fragment thereof) that has significant binding affinity for a molecule on the surface of a target cell (e.g., a tumor cell or an infected cell). The targeting domain will have low or, preferably, substantially no binding affinity for the targeting cell. Thus, for example, where the molecule on the surface of the target cells is a receptor, the targeting domain will be a ligand for the receptor, and where the molecule on the surface of the target cells is a ligand, the targeting domain will be a receptor for the ligand. Thus, targeting domains can be cytokines (e.g., IL-1, IL-2, IL-3, IL-4, IL-5, IL-6, IL-7, IL-8, IL-10, IL-12, IL-13, IL-15, the interferons ($\alpha$, $\beta$, and $\gamma$), TNF-$\alpha$, vascular endothelial growth factor (VEGF), and epidermal growth factor (EGF)) colony stimulating factors (e.g., GM-CSF), hormones (e.g., insulin, or growth hormone), ligands for signal transduction receptors (e.g., CD40 ligand, an MHC class I molecule or fragments of an MHC molecule involved in binding to CD8, an MHC class II molecule or the fragment of an MHC class II molecule involved in binding to CD4), or ligands for adhesion receptors, e.g., ICAM-1, ICAM-2, or fibronectin or a domain (e.g., one containing one or more of the "Arg-Gly-Asp" repeats) of fibronectin involved in binding to integrin molecules. While the invention does not include as targeting domains antibodies specific for a cell surface molecule on the surface of target cells, it does include as targeting domains immunoglobulin (Ig) molecules of irrelevant specificity (or immunoglobulin molecule fragments that include an Fc portion) that can bind to an Fc receptor (FcR) on the surface of a target cell (e.g., a tumor cell). In addition, in certain B cell lymphomas, the specificity of the cell surface Ig molecules has been defined. Thus, where such B cell lymphoma cells are the target cells, an immunotoxin of the invention could include, as the targeting domain, the antigen or a fragment containing the relevant antigenic determinant for which the surface Ig on the lymphoma cells is specific and thus has significant binding affinity. Such a strategy can also be used to kill B cells which are involved in the pathology of an autoimmune disease (e.g., systemic lupus erythematosus (SLE) or myasthenia gravis (MG)) and which express on their surface an Ig receptor specific for an autoantigen.

Similarly, malignant T cells expressing a cell surface receptor (TCR) of known specificity or autoreactive T cells expressing a cell surface receptor of known specificity and involved in the pathology of an autoimmune disease (e.g., RA, IDDM, MS, SLE, or MG) can be killed with a fusion protein containing, as the targeting domain, a soluble MHC (class I or class II) molecule, an active (i.e., TCR-binding) fragment of such a molecule, or a multimer (e.g., a dimer, trimer, tetramer, pentamer, or hexamer) of either the MHC molecule or the active fragment, containing within its antigenic peptide-binding cleft, an appropriate antigenic peptide (e.g., a peptide fragment of collagen in the case of RA, a peptide fragment of insulin in IDDM, or a peptide fragment of myelin basic protein in MS). Tetramers of MHC class I molecules containing an HIV-1-derived or an influenza virus-derived peptide have been shown to bind to CD8+ T cells of the appropriate specificity [Altman et al. (1996), Science 274:94–96; Ogg et al. (1998), Science 279:2103–2106], and corresponding MHC class II multimers would be expected to be similarly useful with CD4+ T cells. Such complexes could be produced by chemical cross-linking of purified MHC class II molecules assembled in the presence of a peptide of interest or by modification of already established recombinant techniques for the production of MHC class II molecules containing a single defined peptide [Kazono et al. (1994), Nature 369:151–154; Gauthier et al. (1998), Proc. Natl. Acad. Sci. U.S.A. 95:11828–11833]. The MHC class II molecule monomers of such multimers can be native molecules composed of full-length $\alpha$ and $\beta$ chains. Alternatively, they can be molecules containing either the extracellular domains of the $\alpha$ and $\beta$ chains or the $\alpha$ and $\beta$ chain domains that form the "walls" and "floor" of the peptide-binding cleft.

In addition, the targeting domain could be a polypeptide or functional fragment that binds to a molecule produced by or whose expression is induced by a microorganism infecting a target cell. Thus, for example, where the target cell is infected by HIV, the targeting domain could be an HIV envelope glycoprotein binding molecule such as CD4, CCR4, CCR5, or a functional fragment of any of these.

The invention also includes artificial targeting domains. Thus, for example, a targeting domain can contain one or more different polypeptides, or functional fragments thereof, that bind to a target cell of interest. Thus, for example, a given targeting domain could contain whole or subregions of both IL-2 and IL-4 molecules or both CD4 and CCR4 molecules. The subregions selected would be those involved in binding to the target cell of interest. Methods of identifying such "binding" subregions are known in the art. In addition, a particular binding domain can contain one or more (e.g., 2, 3, 4, 6, 8, 10, 15, or 20) repeats of one or more (e.g., 2, 3, 4, 6, 8, 15, or 20) binding subregions of one or more (e.g., 2, 3, 4, or 6) polypeptides that bind to a target cell of interest.

Particularly useful as coding sequences for targeting domains are those whose nucleotide sequences have been defined and made public. Indeed, the nucleotide sequences encoding substantially all the polypeptides listed above have been defined and are available to the public in, for example, scientific publications or data bases accessible to the public by mail or the internet. For example, the nucleic acid sequences (and references disclosing them) encoding the following polypeptides were obtained from GenBank at the National Center for Biotechnology Information, National Library of Medicine, Bethesda, Md.: human IL-1$\alpha$ [Gubler et al. (1986) J. Immunol. 136(7):2492–2497]; human IL-3 [Yang et al. (1986) Cell 47(1):3–10]; human IL-4 (genomic DNA sequence) [Arai et al. (1989) J. Immunol. 142(1): 274–282]; human IL-4 (cDNA sequence) [Yokota et al. (1986) Proc. Natl. Acad. Sci. U.S.A. 83(16):5894–5898]; human GM-CSF [Wong et al. (1985) Science 228(4701): 81–815]; human VEGF [Weindel et al. (1992) Biochem. Biophys. Res. Comm. 183(3):1167–1174]; human EGF [Bell et al. (1986) Nucleic Acids Res. 14(21):8427–8446]; and human CD40 ligand [Graf et al. (1992) Eur. J. Immunol. 22(12):3191–3194].

However, the invention is not limited to the use of targeting domains whose nucleotide sequences are currently available. Methods of cloning nucleic acid molecules encoding polypeptides and establishing their nucleotide sequences are known in the art [e.g., Maniatis et al., Molecular Cloning: A Laboratory Manual (Cold Spring Harbor Laboratory, N.Y., 1989) and Ausubel et al. Current Protocols in Molecular Biology (Green Publishing Associates and Wiley Interscience, N.Y., 1989)]

B.2 Toxic Domains

Toxic domains useful in the invention can be any toxic polypeptide that mediates a cytotoxic effect within the cytoplasm of a cell. Preferred toxic polypeptides include ribosome inactivating proteins, e.g., plant toxins such as an A chain toxin (e.g., ricin A chain), saporin, bryodin, gelonin, abrin, or pokeweed antiviral protein (PAP), fungal toxins such as α-sarcin, aspergillin, or restrictocin, bacterial toxins such as DT or *Pseudomonas* exotoxin A, or a ribonuclease such as placental ribonuclease or angiogenin. As with the targeting domains, the invention includes the use of functional fragments of any of the polypeptides. Furthermore, a particular toxic domain can include one or more (e.g., 2, 3, 4, or 6) of the toxins or functional fragments of the toxins. In addition, more than one functional fragment (e.g. 2, 3, 4, 6, 8, 10, 15, or 20) of one or more (e.g., 2, 3, 4, or 6) toxins can be included in the toxic domain. Where repeats are included, they can be immediately adjacent to each other, separated by one or more targeting fragments, or separated by a linker peptide as described above.

Particularly useful as coding sequences for toxic domains are those whose nucleotide sequences have been defined and made public. Indeed, the nucleotide sequences encoding many of the toxic polypeptides listed above have been defined and are available to the public. For example, the nucleic acid sequences (and references disclosing them) encoding the following toxic polypeptides were obtained from GenBank at the National Center for Biotechnology Information, National Library of Medicine, Bethesda, Md.: gelonin [Nolan et al. (1993) Gene 134(2):223–227]; saporin [Fordham-Skelton et al. (1991) Mol. Gen. Genet. 229(3); 460–466]; ricin A-chain [Shire et al. (1990) Gene 93:183–188]; α-sarcin [Oka et al. (1990) Nucleic Acids Res. 18(7):1897]; restrictocin [Lamy et al. (1991) Mol. Microbiol. 5(7):1811–1815]; and angiogenin [Kurachi et al. (1985) Biochemistry 24(20):5494–5499].

However, the invention is not limited to the use of toxic domains whose nucleotide sequences are currently available. Methods of cloning nucleic sequences encoding known polypeptides and establishing their nucleotide sequences are known in the art. [Maniatis et al., supra, Ausubel et al., supra]

C. Expression Vectors

In the expression vectors of the invention, the nucleic acid sequence encoding a fusion protein of interest with an initiator methionine and, preferably, a signal sequence is "operably linked" to one or more transcriptional regulatory elements (TRE), e.g., a promoter or enhancer-promoter combination. "Operably linked" as used herein means that the TRE is in the correct location with respect to the coding nucleic acid sequence to control RNA polymerase initiation and expression of the coding nucleic acid sequence.

A promoter is a TRE composed of a region of a DNA molecule, typically within 100 nucleotide pairs upstream of the point at which transcription starts. Promoters are clustered around the initiation site for RNA polymerase II. Enhancers provide expression specificity in terms of time, location, and level. Unlike a promoter, an enhancer can function when located at variable distances from the transcription site, provided a promoter is present. An enhancer can also be located downstream of the transcription initiation site. The coding sequence in the expression vector is operatively linked to a transcription terminating region. To bring a coding sequence under the control of a promoter, it is necessary to position the translation initiation site of the translational reading frame of the peptide or polypeptide between one and about fifty nucleotides downstream (3') of the promoter. A list of promoters is provided in Table 1.

TABLE 1

| PROMOTERS | | |
|---|---|---|
| PROMOTER TYPE | PROMOTER ELEMENT | REFERENCES |
| CONSTITUTIVE | β-actin | Liu et al., Mol. Cell Biol. 10:3432–40 (1990) |
| | tubulin | Angelichio et al., Nucleic Acids Res. 19:5037–43 (1991) |
| | CMV | see Invitrogen |
| | SV40 enhancer | see Pharmacia |
| | RSV-LTR | see Invitrogen |
| | Adenovirus enhancer | Inoue et al., Biochem Biophys Res Commun 173:1311–6 (1990) |
| TISSUE-SPECIFIC | | |
| LIVER | serum amyloid A | Li et al., Nucleic Acids Res 20:4765–72 (1992) |
| | phenylalanine hydroxylase | Wang et al., J Biol Chem 269:9137–46 (1994) |
| | IGFBP-1 | Babajko et al., PNAS 90:272–6 (1993) |
| | apolipoprotein B | Brooks et al., Mol Cell Biol 14:2243–56 (1994) |
| | albumin | Pinkert et al., Genes Dev 1:268–76 (1987) |
| | vitellogenin | Corthesy et al., Mol Endocrinol 5:159–69 (1991) |
| | angiotensinogen | Brasier et al., Embo J 9:3933–44 (1990) |
| | haptoglobin | Yang et al., Genomics 18:374–80 (1993) |
| | PEPCK | Short et al., Mol Cell Biol 12:1007–20 (1992) |
| | factor IX | Jallat et al., Embo J 9:3295–301 (1990) |
| | transferrin | Idzerda et al., Mol Cell Biol 9:5154–62 (1989) |
| | β-fibrinogen | Dalmon et al., Mol Cell Biol 13:1183–93 (1993) |
| | kininogen | Chen et al., Mol Cell Biol 13:6766–77 (1993) |
| | CRP | Toniatti et al., Mol Biol Med 7:199–212 (1990) |
| KIDNEY | renin | Fukamizu et al., Biochem Biophys Res Commun 199:183–90 (1994) |
| HEART | cardiac myosin light chain | Lee et al., J Biol Chem 267:15875–85 (1992) |
| | cardiac troponin C | Parmacek et al., Mol Cell Biol 12:1967–76 (1992) |
| | α-cardiac myosin heavy chain | Gulick et al., J Biol Chem 266:9180–5 (1991) |
| | MCK | Johnson et al., Mol Cell Biol 9:3393–9 (1989) |
| | troponin I | |
| | atrial natriuretic factor | Rockman et al., PNAS 88:8277–81 (1991) erratum 88(21):9907 |
| LUNG | pulmonary surfactant protein SP-C | Glasser et al., Am J Physiol L349–56 (1991) |
| PANCREAS/ISLET | insulin | Dandoy et al., Nucleic Acids Res 19:4925–30 (1991); and Selden et al., Nature 321:525–8 (1986) |
| | pancreatic amylase | Osborn et al., Mol Cell Biol 7:326–34 (1987) |
| BRAIN/GLIA | GFAP | Brenner et al., J Neurosci 1030–7 (1994) |
| | JCV | Henson et al., J Biol Chem 269:1046–50 (1994) |
| | MBP | Miskimins et al., Brain |

TABLE 1-continued

PROMOTERS

| PROMOTER TYPE | PROMOTER ELEMENT | REFERENCES |
|---|---|---|
| | | Res Dev Brain Res 65:217–21 (1992) |
| | serotonin 2 receptor | Ding et al., Brain Res Mol Brain Res 20:181–91 (1993) |
| | myelin PO | Monuki et al., Mech Dev 42:15–32 (1993) |
| | myelin proteolipid protein | Berndt et al. J Biol Chem 267:14730–7 (1992) |
| INDUCIBLE | | |
| A) IMMUNE SYSTEM/ NATURAL | IL-2 | Thompson et al., Mol Cell Biol 12:1043–53 (1992) |
| | IL-4 | Todd et al., J Exp Med 177:1663–74 (1993) |
| | IL-6 | Libermann et al., Mol Cell Biol 10:2327–34 (1990); and Matsusaka et al., PNAS 90:10193–7 (1993) |
| | IL-8 | Matsusaka et al., PNAS 90:10193–7 (1993) |
| | IL-10 | Kim et al., J Immunol 148:3618–23 (1992) |
| | TNF-α | Drouet et al., J Immunol 147:1694–700 (1991) |
| | IL-1 | Shirakawa et al., Mol Cell Biol 13:1332–44 (1993) |
| | MIP-1 | Grove et al., Mol Cell Biol 13:5276–89 (1993) |
| | IFN-γ | Penix et al., J Exp Med 178:1483–96 (1993) |
| | VCAM-1 | Iademarco et al., J Biol Chem 267:16323–9 (1992) |
| | ICAM-1 | Voraberger et al., J Immunol 147:2777–86 (1991) |
| | ELAM-1 | Whelan et al., Nucleic Acids Res 19:2645–53 (1991) |
| | tissue factor | Mackman et al., J Exp Med 174:1517–26 (1991) |
| | IFN-β | Visvanathan et al., Embo J 8:1129–38 (1989) |
| | c-jun | Muegge et al., PNAS 90:7054–8 (1993) |
| | junB | Nakajima et al., Mol Cell Biol 13:3017–41 (1993) |
| | c-fos | Morgan et al., Cell Prolif 25:205–15 (1992) |
| | iNOS | Xie et al., J Exp Med 177:1779–84 (1993) |
| | G-CSF | Shannon et al., Growth Factors 7:181–93 (1992) |
| | GM-CSF | Miyatake et al., Mol Cell Biol 11:5894–901 (1991) |
| B) IMMUNE SYSTEM/ SYNTHETIC multiple copies of binding sites | NF-KB | Lenardo et al., Cell 58:227–9 (1989) |
| | NF-IL6 | Akira et al., Embo J 9:1897–906 (1990) |
| | IL6-response element | Wegenka et al., Mol Cell Biol 13:276–88 (1993) |
| | CRE | Brindle et al., Curr Opin Genet Dev 2:199–204 (1992) |
| | AP-1 | Auwerx et al., Oncogene 7:2271–80 (1992) |
| | p91/stat combinations of multiple NF-KB and NF-IL6 or combinations with the other elements | Larner et al., Science 261:1730–3 (1993) |
| C) EXOGENOUS/ NON- MAMMALIAN | IPTG inducible/lac repressor/operon system | see Stratagene LacSwitch ™, La Jolla, CA |
| | ecdysone-inducible promoter/ecdysone receptor | Burtis et al., Cell 61:85–99 (1990) |
| | Na-salicylate- inducible promoter PG/regulator nahR | Yen, J Bacteriol 173:5328–35 (1991) |
| | nalidixic acid inducible recA promoter | Rangwala et al., Biotechnology 9:477–9 (1993) |

Suitable expression vectors include, without limitation, plasmids and viral vectors such as herpes viruses, retroviruses, vaccinia viruses, attenuated vaccinia viruses, canary pox viruses, adenoviruses, adeno-associated viruses, lentiviruses and herpes viruses, among others.

The expression vectors of the invention containing the above described coding sequences have a variety of uses. They can be used, for example, to transfect or transduce either prokaryotic (e.g., bacteria) cells or eukaryotic cells (e.g., yeast, insect, or mammalian) cells. Such cells can then be used, for example, for large or small scale in vitro production of the relevant fusion protein by methods known in the art. The transduced/transfected cells can be used as targeting cells for delivery of the immunotoxic protein to a target cell by administration of the transduced/transfected cells to a subject harboring the target cell (see below). Alternatively, the vector itself can be delivered to the subject (see below).

D. Administration of an Immunotoxic Fusion Protein

The immunotoxic fusion proteins of the invention can be delivered to a cell population in vitro in order, for example, to deplete the population of cells expressing a cell surface molecule to which the targeting domain of an appropriate fusion protein binds. For example, the population of cells can be bone marrow cells from which it desired to remove contaminating tumor cells prior to use of the bone marrow cells for autologous bone marrow transplantation in a cancer patient. In such in vitro administrations, either the isolated fusion protein itself, an expression vector encoding the fusion protein, or cells transduced or transfected with an expressing vector encoding the fusion protein can be added to the cell population. The mixture is cultured to allow for production of the immunotoxin (where the vector or genetically manipulated targeting cells are added), binding of the immunotoxin to the tumor cells, and killing of the tumor cells.

Alternatively, a fusion protein can be administered to a subject in which it is desired to eliminate a cell population expressing a cell surface molecule to which the targeting domain of the fusion protein binds. Appropriate subjects include, without limitation, those with any of a variety of tumors (e.g., hematological cancers such as leukemias and lymphomas, neurological tumors such as astrocytomas or glioblastomas, melanoma, breast cancer, lung cancer, head and neck cancer, gastrointestinal tumors, genitourinary tumors, and ovarian tumors, bone tumors, vascular tissue tumors), those with any of a variety of autoimmune diseases (e.g., RA, IDDM, MS, MG, or SLE), or those with an infectious disease involving an intracellular microorganism (e.g., *Mycobacterium tuberculosis, Salmonella*, influenza virus, measles virus, hepatitis C virus, human immunodeficiency virus, and *Plasmodium falciparum*). In the case of a tumor, the fusion protein is delivered to the tumor cells, thereby resulting in the death of a substantial number, if not all the tumor cells. In the case of infection, the fusion protein is delivered to the infected cells, thereby resulting in the death of a substantial number of, in not all, the cells and thus a substantial decrease in the number of, if not total elimination of, the microorganisms. In autoimmune diseases, the fusion protein can contain a targeting domain directed at the T cells (CD4+ and/or CD8+) and/or B cells producing antibodies that are involved in the tissue destructive immune responses of the diseases.

Subjects receiving such treatment can be any mammal, e.g., a human (e.g., a human cancer patient), a non-human primate (e.g., a chimpanzee, a baboon, or a rhesus monkey), a horse, a pig, a sheep, a goat, a bovine animal (e.g., a cow or a bull), a dog, a cat, a rabbit, a rat, a hamster, a guinea pig, or a mouse.

These methods of the invention fall into 2 basic classes, i.e., those using in vivo approaches and those using ex vivo approaches.

D.1 In Vivo Approaches

In an in vivo approach, an expression vector containing a nucleic acid sequence encoding the immunotoxic fusion protein can be delivered to an appropriate cell of the subject. Expression vectors and genetic constructs can be any of those described above. Expression vectors can be administered systemically to a subject. However, expression of the coding sequence will preferably be directed to a tissue or organ of the subject containing the target cells. For example, an appropriate expression vector can be delivered directly to a tumor or, at the time of surgery, to tissues in the region of the body of the subject from which the tumor was surgically removed. Similarly, expression vectors can be delivered directly to the site of an infection or an autoimmune attack, e.g., joints in RA or the pancreas in IDDM. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1–10 μm in diameter can be used. The expression vector is encapsulated in these microparticles, which are taken up by macrophages and gradually biodegraded within the cell, thereby releasing the expression vector. Once released, the expression vector is expressed within the cell. A second type of microparticle is intended not to be taken up directly by cells, but rather to serve primarily as a slow-release reservoir of expression vector that is taken up by cells only upon release from the microparticle through biodegradation. These polymeric particles should therefore be large enough to preclude phagocytosis (i.e., larger than 5 μm and preferably larger than 20 μm). Microparticles useful for nucleic acid delivery, methods for making them, and methods of use are described in greater detail in U.S. Pat. No. 5,783,567, incorporated herein by reference in its entirety.

Another way to achieve uptake of vectors is through the use of liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, tissue specific targeting can be achieved by the use of tissue-specific TRE. A variety of tissue specific TRE and relevant references are listed in Table 1.

Expression vectors can be administered in a pharmaceutically acceptable carrier. Pharmaceutically acceptable carriers are biologically compatible vehicles suitable for administration to a mammalian subject such as, for example, a human patient, e.g., physiological saline. A therapeutically effective amount is an amount of the expression vector which is capable of producing a medically desirable result in a treated mammal, e.g., a human patient. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of an expression vector is from approximately $10^6$ to $10^{12}$ copies of the expression vector. This dose can be repeatedly administered, as needed. Routes of administration include, without limitation, intramuscular, intravenous, subcutaneous, intraperitoneal, intrarectal, intravaginal, intranasal, intragastric, intratracheal, or intrapulmonary routes. In addition, administration can be oral or transdermal, employing a penetrant such as a bile salt, a fusidic acid or another detergent. The injections can be single or multiple (e.g., 2-, 3-, 4-, 6-, 8-, or 10- fold).

D.2 Ex Vivo Approaches

An ex vivo strategy can involve transfecting or transducing targeting cells obtained from the subject with an expression vector containing the immunotoxin fusion protein coding sequences described above. The transfected or transduced targeting cells are then returned to the subject, either at the site of the disease or systemically. While such cells would preferably be lymphoid cells (see above), they could also be any of a wide range of types including, without limitation, fibroblasts, bone marrow cells, macrophages, monocytes, dendritic cells, epithelial cells, endothelial cells, keratinocytes, or muscle cells which act as a source of the fusion protein for as long as they survive in the subject. It is, however, preferred that the targeting cells have significant binding affinity for the target pathogenic cell.

The ex vivo methods include the steps of harvesting cells from a subject, culturing the cells, transfecting or transducing them with an expression vector, and maintaining the cells under conditions suitable for expression of the fusion protein. The expression vectors and genetic constructs can be any of those described above. These methods are known in the art of molecular biology. The transfection or transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are optionally selected, for example, for expression of the coding sequence or of a drug resistance gene. The cells may then be lethally irradiated (if desired) and injected or implanted into the patient.

While it is preferred that the targeting cells be autologous (i.e., obtained from the subject to which they are being administered following genetic manipulation), it is understood that they need not be autologous (see section on targeting cells above).

These methods of the invention can be applied to any of the diseases and species listed here. Testing whether a given fusion protein is therapeutic for a particular disease can be by methods known in the art. Where a therapeutic effect is being tested, a test population of subjects displaying signs or symptoms of the disease (e.g., cancer or RA patients) is treated with a test immunotoxic fusion protein, using any of the above described strategies. A control population, also displaying signs or symptoms of the disease, is treated, using the same methodology, with a placebo. Disappearance or a decrease of the disease signs or symptoms in the test subject indicates that the immunotoxic fusion protein is an effective therapeutic agent.

The following examples are meant to illustrate, not limit, the invention.

EXAMPLES

Example 1

Materials and Methods

Genetic Constructs A single chain cytokine nucleic acid sequence encoding full-length murine IL-4 (140 amino acid residues of the full-length polypeptide, including its native 20 amino acid signal peptide) (sigIL-4) was fused in frame with a truncated nucleic acid sequence encoding the first 390 amino acids of DT (DT390) (including the initial methionine and devoid of the native binding region that renders the toxin lethal to all eukaryotic cells), using splice overlap extension [Chan et al. (1995) Blood 86:2732]. The N-terminal IL-4 domain was separated from the DT390 domain by a flexible linker with the amino acid sequence EASGGPE (SEQ ID NO:3). The 1,626 base pair immunotoxin (sigIL-4DT390) coding sequence was ligated into the nonviral mammalian expression vector pcDNA.3 (InVitrogen) as shown in FIG. 1B and was used for transfection studies in NIH.3T3 cells to determine whether mammalian cells can produce targeted toxins. For transduction, the coding sequence was ligated into the retroviral expression vector LNCX (FIG. 1C) or a modified LNCX in which a fragment encoding the neomycin resistance gene (Neo) was replaced with a gene fragment encoding human nerve growth factor receptor (NGFR) (FIG. 1D). Successful integration of this retrovirus resulted in the cell surface expression of NGFR which could be used as a quantitative marker of successful transduction. To produce a purifiable IL-4 immunotoxin, a IL-4 fusion toxin coding sequence was assembled using DNA fragments encoding IL-4 (without its signal sequence) and DT390 by splice overlap extension (FIG. 1A). This coding sequence was ligated into the pet21d expression vector. Recombinant protein (DT390IL-4) was expressed in *E. coli* bacteria, refolded and purified by ion exchange chromatography as previously described [Chan et al. (1996) Blood 88:1445].

Cells, cell lines, and antibodies C1498 is a spontaneously occurring myeloid leukemia which is lethal to mice in 20–30 days [Durham et al. (1953) J. Natl. Canc. Inst. 13:1299; Bradner et al. (1996) Cancer Res. Cancer Chemo. Screen Data 43:375]. T15 is a CD8+ cytotoxic T cell line produced by immunizing C57BL/6 mice with C1498 cells and stimulating T cells from the immunized mice in vitro with C1498 cells. Previous studies show it responds to C1498 cells in vitro and in vivo [Boyer et al. (1997) Blood 89:3477]. LAK cells were generated by culturing C57BL/6 splenocytes in 1000 U/ml IL-2. After 6 days of initial culture, cells were cultured for an additional 48 hours in fresh tissue culture medium containing IL-2 at the same concentration. For studies requiring neutralization of IL-4 fusion toxin, a rat IgG1 anti-mouse IL-4 monoclonal antibody (Mab) (Clone 11B11) was used [Ohara et al. (1988) Proc. Natl. Acad. Ser. USA 85:8221].

Genomic Polymerase Chain Reaction To detect integration of the DT containing immunotoxin provirus into T15 cell genomic DNA, DNA isolated from transduced and control untransduced T15 cells was analyzed by PCR using Taq polymerase (Perkin Elmer, Foster City, Calif.) and primers with the sequences 5'GCGCTGATGATGTTGT-TGAT3' (SEQ ID NO:4) and 5'AAATGGTTGCGTTT-TATG3' (SEQ ID NO:5) corresponding to regions of the DT390 fragment encoding sequence. Amplification in a DNA Thermal Cycler (Perkin Elmer) (30 cycles at 94° C. for 30 seconds, 55° C. for 60 seconds, 72° C. for 120 seconds), produced a 1,170 base pair product.

Transfection, harvesting viral supernatants, and viral transduction For transfection of immunotoxin coding sequences into mammalian cells, coding sequences were cloned into the pcDNA.3 mammalian expression vector (Invitrogen, Carlsbad, Calif.). Cells at a concentration of $2\times10^5$/well in DMEM tissue culture medium supplemented with 10% fetal bovine serum (FBS) were seeded into 6-well tissue culture plates (Costar) and incubated at 37° C., in an atmosphere of 10% $CO_2$, 90% air, until 70% confluent. One ul of DNA (2 ug) was mixed with 6 ul of Lipofectamine (GIBCO, Grand Island, N.Y.) in 200 ul DMEM on ice for 30 minutes which was then added to the washed cells. After 5 hours of incubation at 37° C., one ml of DMEM plus 20% FBS was added and the incubation continued overnight.

For transfection of packaging lines and harvesting of viral supernatant, the PA317 packaging line was transfected by electroporation using a Gene Pulser II (Bio-Rad, Hercules, Calif.). Washed PA317 cells were resuspended in electroporation buffer (EB) (272 mM sucrose, 7 mM $K_2HPO_4$, 1 mM $MgCl_2$) at a concentration of $10^7$ cells in 800 ul EB in an electroporation cuvette. Forty ug plasmid was added to the cell suspension which was then incubated on ice for 10 minutes and then electroporated at 200 volts, 950 ufarads, 200 ohms for 80 msec. The cells were plated in a 100 mm dish containing 10 ml DMEM supplemented with 10% FBS and incubated overnight at 37° C. The supernatant was collected and centrifuged at 2500 rpm for 10 minutes, filtered, and stored at −80° C.

Mouse splenic T cells were enriched using commercial Cellect Mouse T Cell columns (Cytovax Biotechnologies, Edmonton, AB, Canada). LAK cells were generated by incubating C57BL/6 T cells in RPMI 1640 tissue culture medium supplemented with 10% FBS and recombinant murine IL-2 (mIL-2) (1000 U/ml) for 6 days.

For transduction, cells (T15 or LAK) were cultured at 32° C. for 5 hours in 1 ml of culture medium and an additional 1 ml of viral supernatant plus 8 ug/ml polybrene, and 1000 U/ml mIL-2 in 24 well plates; where "spin" transduction was used, the above mixture of cells and virus was centrifuged at 2500 rpm, 32° C. for 1.5 hours, prior to culture. After the 5 hour culture, the cells were transferred to a 100 mm culture dish (Costar) and incubated in RPMI 1640 supplemented with 10% FBS for 24 or 48 hours. Transduction frequency was quantitated by fluorescence flow cytometric analysis of NGFR expressing transduced LAK cells. For transducing the T15 T cell line, T15 cells were cultured in RPMI 1640 culture medium with 10% FBS and 100 U/ml IL-2 and were stimulated every 2–3 weeks with the C1498B7.2 cell line as previously described [Boyer et al. (1997) supra]. The C1498B7.2 cell line consists of C1498 cells stably transfected with, and expressing on their surface, a gene encoding the co-stimulatory B7.2 molecule. The T15 cells were the transduced as described above.

Staining for intracellular immunotoxin Cells were cultured on coverslips and transfected with the pcDNA.3 vector encoding sigIL-4DT390. After 30 hours, coverslips were washed twice with PBS and fixed with 95% ethanol/5% acetic acid at −20° C. for 5 minutes. Fixed cells were washed with PBS, incubated with primary 11B11 anti-IL-4 Mab (diluted 1:50 in 5% BSA/PBS), and then incubated for 1 hour at room temperature. For DT staining, cells were incubated with primary polyclonal anti-DT antiserum and secondary FITC-labeled antibody. Coverslips were washed with PBS three times and incubated with secondary FITC-rabbit anti-rat IgG (Sigma, St. Louis, Mo.) (diluted 1:500) for 45 minutes at room temperature. Coverslips were washed three times and then mounted using a slowFade Light Antifade Kit (Molecular Probes, Eugene, Oreg.). The cells were observed and digitally photographed using a Nikon fluorescent microscope with a spot cam.

Flow cytometric analysis To assess the percentage of cells transduced with the sigIL-4DT390 encoding nucleic acid sequence, transduced and non-transduced T15 and LAK cells were stained with mouse anti-NGFR primary antibody (Boehringer Mannheim, Indianapolis, Ind.) (diluted 1:1000) for 15 minutes at room temperature, and FITC-labelled anti-mouse IgG secondary antibody (Chemicon, Temecula, Calif.) (diluted 1:100) for 15 minutes at room temperature. Samples were analyzed on a FACSCalibur (Becton Dickinson, Franklin Lakes, N.J.) as previously described [Vallera et al. (1996) Blood 88:2342]. Forward and side scatter settings were gated to exclude red cells and debris. 7,000–10,000 cells were analyzed for each determination. T cell, NK cell, and B cell content was measured using CD4, CD8, TCR, CD19, NK1.1 antibodies from PharMingen (San Diego, Calif.) by 2 or 3 color flow cytometry using fluorescein isothiocyanate (FITC), phycoerythrin or biotin- conjugated Mab purchased from PharMingen or Becton-Dickinson (Mountainview, Calif.). Where biotin-conjugated primary Mab were used, the secondary reagent was perCP-conjugated streptavidin (SA). Irrelevant Mab control values were subtracted from values obtained with relevant Mabs.

Viability Assays To assess immunotoxin killing, IL4R+ C1498 cells were plated at $2 \times 10^5$/well in 24 well tissue culture plates (Costar). One ml filtered supernatant from cultured transduced LAK or T15 cells was added to each well. Wells were analyzed at 24, 48, and 72 hours. The cells diluted in trypan blue dye/PBS solution, and the number of surviving cells determined. To assess specificity of killing, supernatants were simultaneously tested on IL4R− EL4 cells.

JAM assay Cytotoxiciy was measured by a modified JAM assay in which target cell proliferation is assessed by thymidine incorporation [Matzinger (1991) J. Immunol. Meth. 145(1–2):185–192]. Briefly, C1498 or EL4 target cells are pulsed for 3.5 hours with tritiated thymidine, washed, and then added to LAK or T15 effector cells in 96 well U-bottomed plates (Costar) at effector:target ratios of 100, 50, 25, 12.5, 6.2, 3.1, and 1.5 to 1. Plates were centrifuged and incubated for an additional 3.5 hours at 37° C. in a humidified atmosphere of 5% $CO_2$ and 95% air. The cells were then harvested and counted by standard scintillation counting techniques.

Percent cytotoxicity=[(background counts-experimental counts)/(background counts-maximally released counts)]×100 where: background counts are the counts obtained in culture wells containing target cells and no effector cells; experimental counts are counts obtained in culture wells containing target cells and the effector cells of interest; and maximally released counts are counts obtained in culture wells containing target cells and detergent.

In vivo studies Two million C1498 cells were injected subcutaneously (s.c.) into the shaved flank of C57BL/6 mice (5–6 week old females purchased from the Jackson Laboratory, Bar Harbor, Me.) housed in a SPF (specific pathogen free) facility at the University of Minnesota. Mice were given an intravenous (i.v.) (caudal vein) injection of either T15 cells transduced with the retroviral vector shown in FIG. 1C, non-transduced T15 cells, or no T15 cells. Since the T15 cell line is dependent on IL-2 for growth, all injections of T15 cells were given in 20,000 U/ml mouse IL-2. Three injections of T15 cells were administered over the period of 11 days. Tumor growth in 3 dimensions was measured almost everyday and tumor volume calculated.

Example 2

Specificity of Tumor Cell Killing by Recombinant DT390IL-4 Purified from a Bacterial Expression System To determine the specificity of an IL-4 fusion immunotoxin against myeloid cancers, the construct shown in FIG. 1A was assembled. The DT390IL-4 fusion protein encoding nucleic acid sequence was expressed in E. coli bacteria from which it was purified. IL-4R+ C1498 leukemia cells were cultured in the presence of various concentrations (0–10 nM) of DT390IL-4. At 24, 48, and 72 hours, cells were stained with trypan blue dye (which stains dead cells) and live cells were counted. FIG. 2A shows that 1.0 nM DT390IL-4 killed all cells by 48 hours. FIG. 2B shows that the addition of anti-Ly5.2, an irrelevant control antibody, which does not bind to C1498 or to DT390IL-4, did not alter activity. However, the addition of 20 uM anti-IL4 Mab (FIG. 2C) blocked C1498 killing at DT390IL-4 concentrations of 1 and 10 nM. In independent experiments, DT390IL-4 killed another IL4R+ myeloid leukemia B162, an IL4R+ glioma and neuroblastoma (data not shown). It did not, however, kill the IL-4R− T cell thymoma EL4. Together, these data indicate that DT390IL-4 killing was specific and the specificity could be attributed to the IL-4 moiety of the immunotoxic fusion protein.

Example 3

Expression of the sigIL-4DT390 Coding Sequence in Mammalian Cells

In order to determine the feasibility of producing cytokine fusion immunotoxins intracellularly, a construct encoding a fusion protein that included the 20 amino acid signal peptide (sigIL-4DT390) was assembled and cloned into the mammalian expression vector pcDNA.3 that contained neo (FIG. 1B). The correct assembly of this and all constructs was confirmed by DNA sequencing. Thirty hours following transfection with sigIL4DT390/pcDNA.3, indirect IF staining revealed definitive intracellular presence of both the DT and the IL-4 moiety of the hybrid protein. No staining was observed in controls transduced with the empty pcDNA.3 vector and stained with anti-DT antibody or with anti-IL-4 antibody. No staining was observed when cells transfected with the sigIL-4DT390 encoding nucleic acid sequence were stained with FITC-labeled secondary antibody without primary antibody, indicating that secondary antibody was not binding non-specifically.

To determine whether expressed protein was secreted, supernatants were collected from an aliquot of these transfected cells. FIG. 3 shows that supernatants collected from cultured NIH.3T3 cells transfected with vector containing the sigIL-4DT390 coding sequence killed C1498 cells, but not control EL4 cells. Control supernatants from NIH.3T3 cells transfected with empty vector did not affect either cell. Control DT390IL-4 at a concentration of $10^{-8}$M inhibited C1498 with the same efficiency as supernatant from cells transfected with the sigIL-4DT390 encoding nucleic acid sequence. Together, these data show that transfection with the sigIL-4DT390 encoding nucleic acid sequence results in the secretion of functional fusion protein toxin that is specifically toxic.

Example 4

Transduction of T15 Cells

In order to be useful for retroviral production of a DT/IL-4 containing immunotoxin, T15 cells cannot be susceptible to killing by such a protein. FIG. 4 shows that the growth of T15 cells was not inhibited (FIG. 4B) by concentrations of DT390IL-4 that killed C1498 (FIG. 4A). Also, fibroblast packaging lines PA317 (FIG. 4D) and GP+E-86 (FIG. 4C) were not killed by DT390IL-4, thus rendering them acceptable hosts for packaging virus containing the sigIL-4DT390 coding sequence.

The in vitro growth of T15 cells is dependent on IL-2 and antigen stimulation by irradiated C1498 cells every 3 weeks. FIG. 5 shows that IL-2 dependent proliferation of T15 cells as measured by [$^3$H]-thymidine uptake was not inhibited by the addition of DT390IL4 and other recombinant cytokine fusion toxins including DT390IL-3, DT390GM-CSF, and DT390. As predicted, proliferation of the T15 cells was inhibited by DT390IL-2.

T15 cells were transduced with viral supernatants from PA317 packaging cells electroporated with the sigIL-4DT390/LNCX retroviral vector (FIG. 1C). Fluorescence microscopy analysis showed that, 30 hours after transduction, a high proportion of the transduced T15 cells expressed intracellular IL-4 and DT. Non-transduced T15 did not express either IL-4 or DT. As a tool for studying transduction frequency, T15 cells were transduced with an LNCX vector in which neo had been replaced with NGFR (FIG. 1D). FIG. 6 shows that transduction with viral supernatants from sigIL-4DT390/LNCX.NGFR-treated packaging cells resulted in cell surface expression of NGFR on T15 cells measurable by flow cytometry. Supernatants were collected from packaging cells at 24, 48, and 72 hours and were used to transduce T15 cells once or twice at various dilutions (FIG. 7). High transduction levels were obtained using a dilution of 1:2, with a decline in transduction efficiency at higher dilutions. Generally, the data indicate that 45–50% cells express the NGFR gene following transduction with 24 or 48 hour supernatants at a dilution of 1:2 using a single transduction. Spin transduction as an additional means to enhance transduction frequency was studied (FIG. 8). In spin transduction, the cells are centrifuged ("spun") at 5,000 g for 1.5 hours in retrovirus containing medium. Cells were spun or not spun, the plate was incubated either for 4 hours or overnight, and the cells were transferred to a 10 mm tissue culture dish which was incubated for either 24 or 48 hours. Spinning T15 cells did not have an affect on the level of transduction.

To determine whether sigIL-4DT390 was secreted from the transduced cells, supernatants were collected from them and tested on either IL4R+ C1498 cells or ILR4− EL4 cells. Growth of C1498 cells was inhibited by supernatant from transduced, but not by supernatant from non-transduced cells (FIG. 9). EL4 cells continued to proliferate despite exposure to supernatants from transduced or non-transduced T15. Control DT390IL4 inhibited C1498, but not EL4. Together, these data show that transduction with the sigIL-4DT390 coding sequence results in the secretion of the specifically toxic fusion protein.

A subline of T15 was produced following transduction with sigIL-4DT390/LNCX and a 2 week selection in G418. FIG. 10 shows the presence of the 1.2 kb DT390 coding sequence in cultured T15 cells as detected by the genomic PCR described in Example 1.

Example 5

Transduction of LAK Cells

An alternative to tumor-specific CTL for delivery of a immunotoxic molecule for cellular immunotherapy are LAK cells which have been shown to home to a variety of tumors. FIG. 11 shows that when LAK cells were transduced with viral supernatant, 30 hours later there was an 18% increase in the level of NGFR expression lymphocytes measured by flow cytometry. FIG. 12 shows that the ability of LAK cells to kill C1498 or EL4 cancer cells in short term cytotoxicity assays was not impaired by the viral transduction procedure. For C1498, cytotoxicity levels were 50–60% in transduced and in non-transduced cells. FIG. 13 shows that the proportion of NGFR+ transduced cells was increased when spin transductions were performed on LAK cells in a manner identical to those performed on T15. FIG. 14 shows that LAK cells secreted functional fusion toxin since supernatants collected from transduced LAK cells selectively killed C1498 cells, but not EL4. Again, control DT390IL-4 was selectively toxic.

Example 6

Inhibition of Tumor Growth by sigIL-4DT390 Encoding T15 Cells in vivo

Mice administered $2\times10^6$ C1498 cells by s.c. injection on day 0 were injected i.v. three times over an 11 day period with the T15 cell populations described in Example 1 (FIG. 15). Each mouse was injected with $27\times10^6$ T15 cells on day 5, $18\times10^6$ T15 cells on day 10, and $30\times10^6$ T15 cells on day 16 after C1498 injection. Tumor size steadily increased in groups of mice given nontransduced T15 cells or in groups of tumor mice that were not treated. In contrast, tumor growth was inhibited until day 18 in mice injected with transduced T15. Following day 18, the tumors began to grow. This experiment indicates that delivery of the sigIL-4DT390 immunotoxin to growing C1498 tumor cells in vivo by transduced CTL, which both recognize the tumor and secrete the immunotoxin, results in a decrease in the rate of tumor growth.

Example 7

ASSEMBLY OF RETROVIRAL IMMUNOTOXINS USING OTHER TOXIN CODING SEQUENCES

The nucleic acid sequence encoding sigIL-4 was spliced to a coding sequence encoding truncated *Pseudomonas* exotoxin (PE) and cloned into LNCX. The PE fragment ("PE40"), which consisted of 327 amino acid residues, lacked domain 1 but contained the translocation domain (domain 2) and the catalytic (toxic) domain (domain 3). Virus (FIG. 16) was produced and used to infect NIH.3T3 cells. The expression of the PE coding sequence in these mammalian cells was verified by intracellular immunofluorescence analysis, as described for the sigIL-4DT390 expressing T15 cells.

Although the invention has been described with reference to the presently preferred embodiment, it should be understood that various modifications can be made without departing from the spirit of the invention. Accordingly, the invention is limited only by the following claims.

What is claimed is:

1. An isolated targeting cell comprising a vector, said vector comprising a nucleic acid sequence encoding a fusion protein, said fusion protein comprising:
   (a) a targeting domain comprising a first member of an affinity pair; and
   (b) a toxic domain comprising a toxic molecule,
   wherein said targeting cell is a T lymphocyte and has significant binding affinity for a cancer cell, said targeting cell expresses and secretes said fusion protein, said first member binds to a second member of said affinity pair, and said second member is expressed on a surface of the cancer cell, and
   wherein said first member is a cytokine, a growth factor, or a colony stimulating factor.

2. The targeting cell of claim 1, wherein said first member is a cytokine.

3. The targeting cell of claim 1, wherein said cytokine, growth factor, or colony stimulating factor is interleukin (IL)-4.

4. The targeting cell of claim 2, wherein said cytokine, growth factor, or colony stimulating factor is selected from the group consisting of IL-1, IL-5, IL-7, IL-8, IL-10, IL-12, IL-15, interferon (IFN)-α, IFN-β, IFN-γ, tumor necrosis factor (TNF)-α, and vascular endothelial growth factor (VEGF).

5. The targeting cell of claim 1, wherein said second member is a receptor for a cytokine, growth factor, or colony stimulating factor.

6. The targeting cell of claim 5, wherein said second member is an IL-4 receptor (IL-4R).

7. The targeting cell of claim 5, wherein said receptor for a cytokine, growth factor, or colony stimulating factor is selected from the group consisting of receptors for IL-1, IL-2, IL-3, IL-5, IL-6, IL-7, IL-8, IL-10, IL-12, IL-13, IL-15, IFN-α, IFN-β, IFN-γ, TNF-α, TGF, GM-CSF, VEGF, and EGF.

8. The targeting cell of claim 1, wherein said cancer cell is a malignant hematological cell.

9. The targeting cell of claim 1, wherein said cancer cell is selected from the group consisting of a neural tissue cancer cell, a melanoma cell, a breast cancer cell, a lung cancer cell, a gastrointestinal cancer cell, an ovarian cancer cell, a testicular cancer cell, a lung cancer cell, a prostate cancer cell, a cervical cancer cell, a bladder cancer cell, a vaginal cancer cell, a liver cancer cell, a renal cancer cell, a bone cancer cell, and a vascular tissue cancer cell.

10. The targeting cell of claim 1, wherein said T lymphocyte is a CD8+ T lymphocyte.

11. The targeting cell of claim 1, wherein said toxic molecule is diphtheria toxin (DT) or a functional fragment of DT.

12. The targeting cell of claim 11, wherein said toxic molecule comprises amino acids 1–390 of DT.

13. The targeting cell of claim 1, wherein said toxic molecule is: (i) a polypeptide selected from the group consisting of ricin, Pseudomonas exotoxin (PE), bryodin, gelonin, α-sarcin, aspergillin, restrictocin, angiogenin, Pseudomonas exotoxin, saporin, abrin, and pokeweed antiviral protein (PAP), or (ii) a functional fragment of the polypeptide of (i).

14. The targeting cell of claim 1, wherein the vector is a retroviral vector.

15. The targeting cell of claim 1, wherein the vector is selected from the group consisting of a plasmid, an adenoviral vector, a adeno-associated viral vector, a vaccinia viral vector, a lentiviral vector, and a herpes viral vector.

16. An isolated population of cells, wherein each of a substantial number of the cells of the population is the targeting cell of claim 1.

17. The targeting cell of claim 1, wherein said vector further comprises a mammalian signal sequence, wherein said mammalian signal sequence is located 5' of the 5' end of said nucleic acid sequence encoding the fusion protein.

18. The targeting cell of claim 17, wherein said signal sequence is a signal sequence encoding a natural leader sequence of said first member.

19. The targeting cell of claim 18, wherein said first member is IL-4.

20. A method of treating a subject with cancer, said method comprising administering said cell population of claim 16 to said subject, wherein the subject comprises the cancer cell for which the targeting cell is specific and on the surface of which the second member of the affinity pair is expressed.

21. A method of making the cell population of claim 16, the method comprising:
   (a) providing a preparation of cells, wherein each of a substantial number of said preparation of cells is a T cell and has significant binding affinity for a cancer cell; and
   (b) transfecting or transducing cells of said preparation of cells with a vector comprising a DNA sequence encoding a fusion protein including:
      (i) a targeting domain comprising a first member of an affinity pair, wherein the first member is a cytokine, a growth factor, or a colony stimulating factor; and
      (ii) a toxic domain comprising a toxic molecule,
   wherein said transfection or said transduction results in the cell population of claim 16.

22. The method of claim 21, further comprising, after said transfection or said transduction, enriching for cells expressing and secreting said fusion protein.

23. The targeting cell of claim 1, wherein said T lymphocyte is a CD4+ T lymphocyte.

24. The targeting cell of claim 1, wherein said cytokine, growth factor, or colony stimulating factor is IL-3.

25. The targeting cell of claim 1, wherein said cytokine, growth factor, or colony stimulating factor is selected from the group consisting of IL-2, IL-6, IL-13, a transforming growth factor (TGF), granulocyte-macrophage colony stimulating factor (GM-CSF), and epidermal growth factor (EGF).

* * * * *

```
                          SEQUENCE LISTING

<160> NUMBER OF SEQ ID NOS: 5

<210> SEQ ID NO 1
<211> LENGTH: 25
<212> TYPE: PRT
<213> ORGANISM: Homo sapiens

<400> SEQUENCE: 1

Met Ala Ile Ser Gly Val Pro Val Leu Gly Phe Phe Ile Ile Ala Val
 1               5                  10                  15

Leu Met Ser Ala Gln Glu Ser Trp Ala
            20                  25

<210> SEQ ID NO 2
<211> LENGTH: 4
<212> TYPE: PRT
<213> ORGANISM: Rattus norvegicus

<400> SEQUENCE: 2

Lys Asp Glu Leu
 1

<210> SEQ ID NO 3
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 3

Glu Ala Ser Gly Gly Pro Glu
 1               5

<210> SEQ ID NO 4
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 4
gcgctgatga tgttgttgat                                                20

<210> SEQ ID NO 5
<211> LENGTH: 18
<212> TYPE: DNA
```

```
-continued

<213> ORGANISM: Artificial Sequence
<220> FEATURE:
<223> OTHER INFORMATION: Synthetically generated oligonucleotide

<400> SEQUENCE: 5
aaatggttgc gttttatg                                                     18
```